United States Patent
Yeung et al.

(10) Patent No.: US 11,826,425 B2
(45) Date of Patent: Nov. 28, 2023

(54) COMPOSITIONS AND METHODS FOR TREATMENT OF ENTEROVIRUS INFECTION

(71) Applicant: VERSITECH LIMITED, Pokfulam (HK)

(72) Inventors: Philip Man Lung Yeung, Kowloon (HK); Fuk Woo Jasper Chan, Kowloon (HK); Manson Fok, Mid-Levels Central (HK); Johnson Yiu-Nam Lau, Houston, TX (US); Kwok-Yung Yuen, Pokfulam (HK)

(73) Assignee: VERSITECH LIMITED, Hong Kong (CN)

( * ) Notice: Subject to any disclaimer, the term of this patent is extended or adjusted under 35 U.S.C. 154(b) by 0 days.

(21) Appl. No.: 16/333,114

(22) PCT Filed: Sep. 13, 2017

(86) PCT No.: PCT/US2017/051391
§ 371 (c)(1),
(2) Date: Mar. 13, 2019

(87) PCT Pub. No.: WO2018/053019
PCT Pub. Date: Mar. 22, 2018

(65) Prior Publication Data
US 2019/0358326 A1 Nov. 28, 2019

Related U.S. Application Data

(60) Provisional application No. 62/394,061, filed on Sep. 13, 2016.

(51) Int. Cl.
*A61K 39/42* (2006.01)
*A61P 31/12* (2006.01)
(Continued)

(52) U.S. Cl.
CPC ............. *A61K 39/42* (2013.01); *A61P 31/12* (2018.01); *C07K 16/40* (2013.01); *A61K 2039/57* (2013.01)

(58) Field of Classification Search
None
See application file for complete search history.

(56) References Cited

U.S. PATENT DOCUMENTS 8,263,570 B2   9/2012   Ho et al.
2014/0023732 A1   1/2014   Cao et al.
(Continued)

FOREIGN PATENT DOCUMENTS

WO   2008148149   12/2008
WO   2012060779   5/2012
(Continued)

OTHER PUBLICATIONS

Perlman and Gallagher (Journal of Clinical Investigation. Nov. 2018; 128 (11): 4767-4769).*
(Continued)

*Primary Examiner* — Shanon A. Foley
(74) *Attorney, Agent, or Firm* — PABST PATENT GROUP LLP

(57) ABSTRACT

Enteroviruses, such as EV-A71, have been found to utilize hWARS as a cell surface receptor, with expression of hWARS rendering cells susceptible to enteroviral infection. Reduction in hWARS cell surface activity reduces susceptibility to enteroviral infection and provides a mode for treatment or prevention of enteroviral infection and its sequelae. Similarly, expression of hWARS in cultured cells and animal models provides models for understanding enteroviral disease mechanisms and the development of
(Continued)

vaccines and/or pharmaceuticals for preventing or treating enteroviral disease.

12 Claims, 12 Drawing Sheets

Specification includes a Sequence Listing.

(51) Int. Cl.
    *C07K 16/40*      (2006.01)
    *A61K 39/00*      (2006.01)

(56) References Cited

U.S. PATENT DOCUMENTS

2016/0333075 A1   11/2016   Cardosa
2019/0358326 A1*  11/2019   Yeung .................. A61K 39/42

FOREIGN PATENT DOCUMENTS

WO      2013032404      3/2013
WO      2016137280      9/2016

OTHER PUBLICATIONS

Jin (Experimental and Molecular Medicine. 2019; 51 (1): oi.org/10.1038/s12276-018-0196-9).*
Chen et al. (Frontiers in Microbiology. Feb. 2020; 11 (Article 261: 1-15).*
Fieldhouse et al. (Emerging Microbes and Infections. 2018; 7 (164): DOI 10.1038/s41426-018-0159-1).*
Paley et al. (Molecular Immunobiology. 2007; 44: 541-557).*
Lee et al. (Journal of Virology. Jan. 2019; 9 (2): e01291-18.*
Lim and Poh (Therapeutic Advances in Vaccines and Immunotherapy. 2019; 7: 1-10).*
Laajala et al. (Expert Opinion on Theraputic Targets. 2020; 24 (8): 745-757).*
Hjelm et al. (New Biotechnology. May 2010; 27 (2): 129-137).*
www.ncbi.nlm.nih.gov/geo/query/acc.cgi?acc=GSE80407: 2 pages accessed Jul. 13, 2021.*
Fang et al. (Expert Opinion on Drug Discovery. 2022; 17 (1): 27-39).*
Vermillion et al. (Journal of Virology. (2022): e00833-22).*
Chen et al. (mBio (2022): e01166-22).*
Hu et al. (Viruses 2023; 15: 785).*
Mascarenhas AP, Musier-Forsyth K. The capsid protein of human immunodeficiency virus: interactions of HIV-1 capsid with host protein factors. FEBS J. 2009;276(21):6118-6127. doi:10.1111/j.1742-4658.2009.07315.x.
Guo, Fei, et al. "Specific Inhibition of the Synthesis of Human Lysyl-tRNA Synthetase Results in Decreases in tRNALys Incorporation, tRNA3LysAnnealing to Viral RNA, and Viral Infectivity in Human Immunodeficiency Virus Type 1," Journal of Virology Aug. 2003, 77 (18) 9817-9822; DOI: 10.1128/JVI.77.18.9817-9822.2003.
Cen, Shan, et al. "Retrovirus-Specific Packaging of Aminoacyl-tRNA Synthetases with Cognate Primer tRNAs," Journal of Virology Dec. 2002, 76 (24) 13111-13115; DOI: 10.1128/JVI.76.24.13111-13115.2002.
Yeung, Man-Lung, et al. "Human tryptophanyl-tRNA synthetase is an IFN-γ-inducible entry factor for Enterovirus," J Clin Invest. 2018;128(11):5163-5177. https://doi.org/10.1172/JCI99411.
PCT Search Report & Written Opinion dated Dec. 26, 2017 for PCT/US2017/051391 filed on Sep. 13, 2017 in the name of EV71 (HK) Limited (13 pages).
Andreev . D. E. et al., Glycyl-tRNA synthe tase specifically binds to the poliovirus IRES to activate translation initiation; Nuclei c Acids Research, 2012, vol. 40, No. 12, pp. 5602-5614.
Hurdle, J. G. e t al., Prospects for aminoacyl-tRNA synthetase inhibitors as new antimicrobial agents, Antimicrobial Agents and Chemotherapy , 2005, vol. 49, No. 12, pp. 4821-4833.
Lee, C.-W. et al., Overexpressed tryptophanyl-tRNA synthetase, an angiostatic protein, enhances oral cancer cell invasiveness, Oncotarget, 2015, vol. 6, No. 26, pp. 21979-21992.
Guo , F. et al., Spec ific inhibition of the synthesis of human lysyl-tRNA synthetase results in decreases in tRNALys incorporation, tRNA3Lys annealing to viral RNA, and viral infectivity in human immunodeficiency virus type 1, Journal of Virology, 2003, vol. 77. No. 18 , pp. 9817-9822.

* cited by examiner

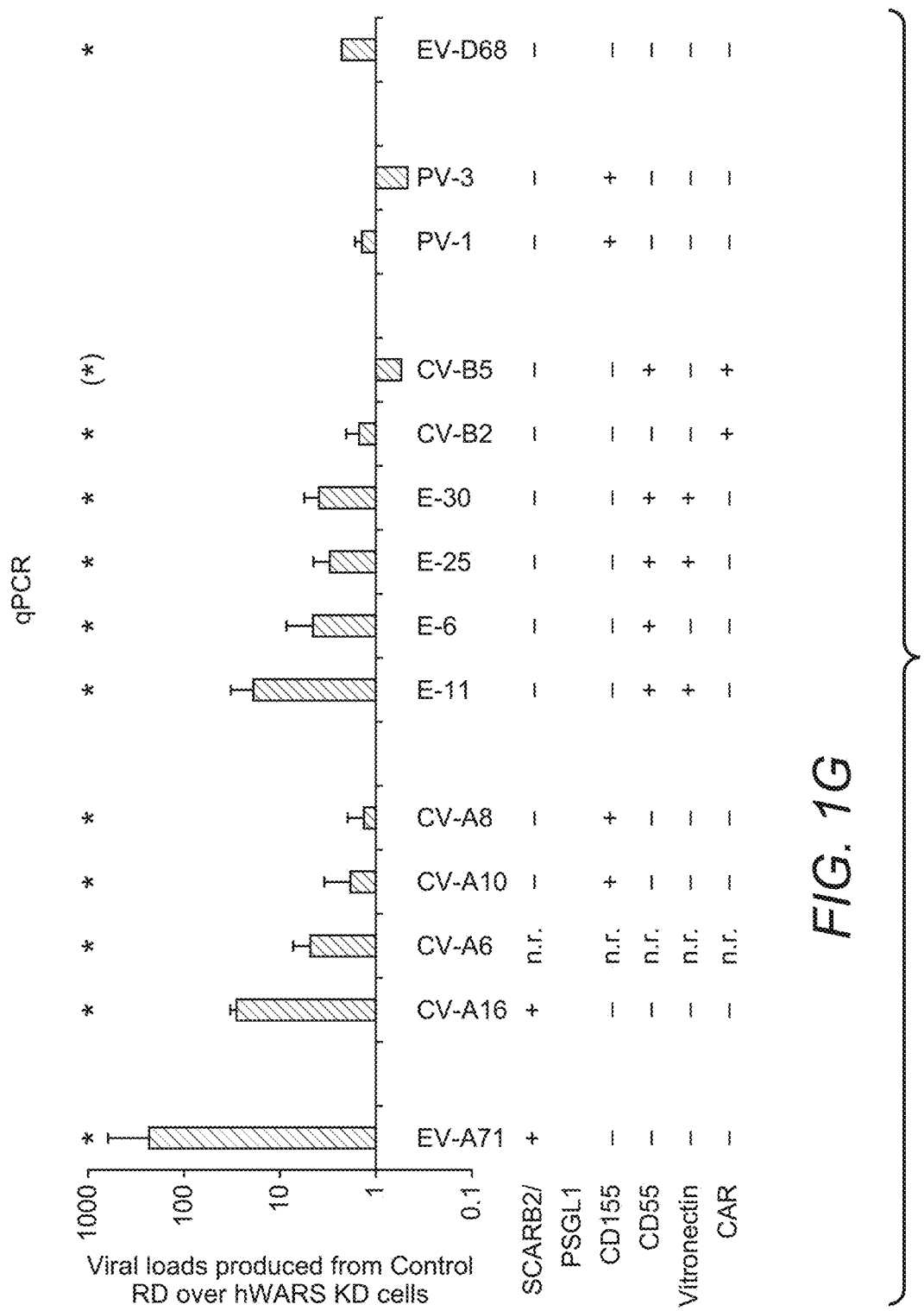

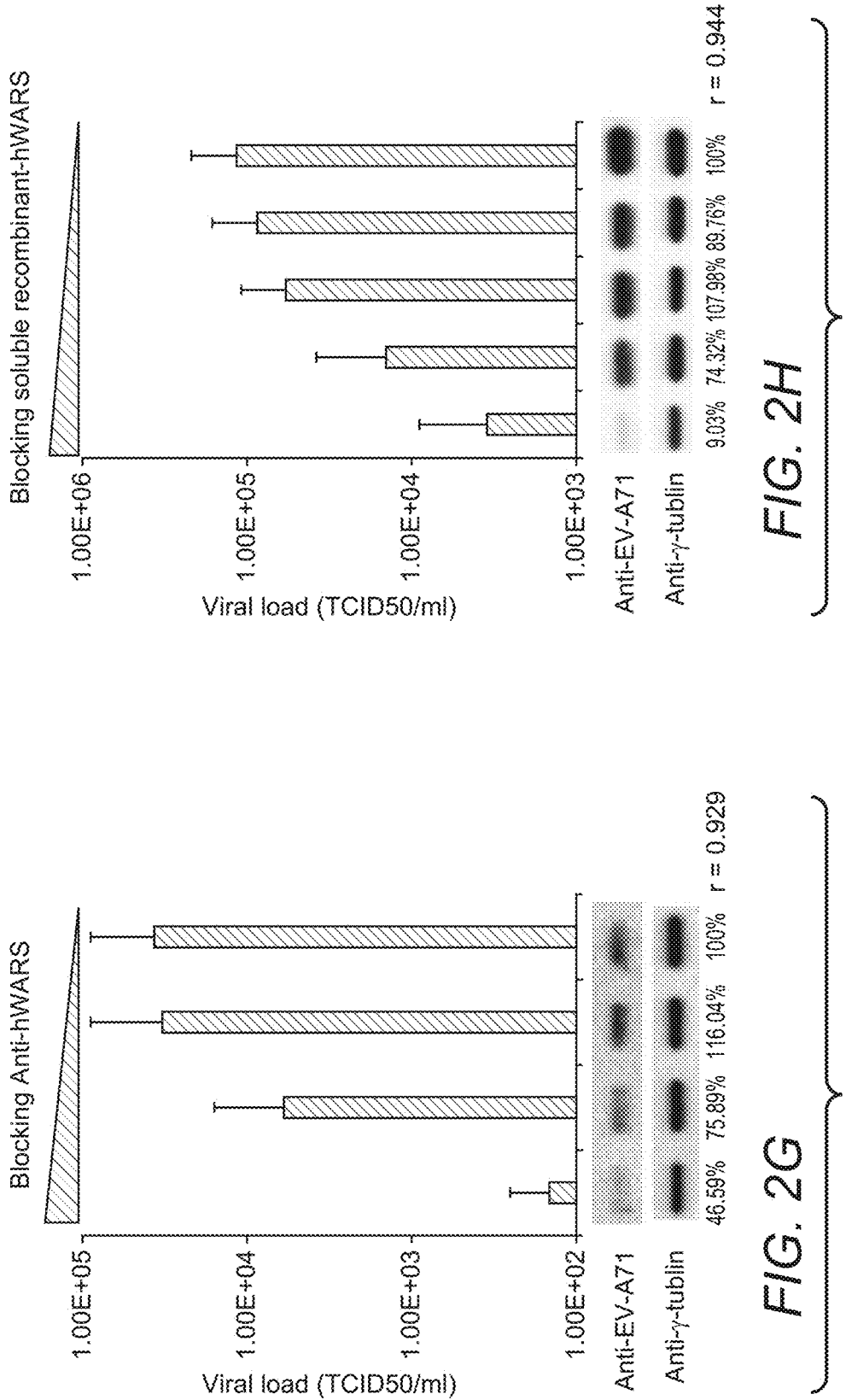

US 11,826,425 B2

COMPOSITIONS AND METHODS FOR TREATMENT OF ENTEROVIRUS INFECTION

This application claims priority to U.S. Provisional Application No. 62/394,061, filed on Sep. 13, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

The Sequence Listing submitted Jan. 19, 2022, as a text file named "UHK_00695_ST25.txt," created on Nov. 21, 2021, and having a size of 3,812 bytes is hereby incorporated by reference pursuant to 37 C.F.R. § 1.52(e)(5).

FIELD OF THE INVENTION

The field of the invention is compositions and methods useful for the treatment of enterovirus infections, particularly enterovirus 71.

BACKGROUND

The background description includes information that can be useful in understanding the present invention. It is not an admission that any of the information provided herein is prior art or relevant to the presently claimed invention, or that any publication specifically or implicitly referenced is prior art.

Enteroviruses are a diverse group of positive-sense single-stranded RNA viruses that are responsible for a number of human and animal diseases, which are typically spread by the fecal-oral route. Such diseases include poliomyelitis, aseptic meningitis, pericarditis/myocarditis, and hand, foot, and mouth disease. A number of enterovirus species are associated with hand, foot, and mouth disease. Some of these (for example, coxsackie virus A16) produce relatively mild symptoms, whereas other species (notably EV-A71) are associated with the development of severe complications, including brainstem encephalitis, aseptic meningitis, pulmonary edema, and cardio-respiratory collapse.

To date treatment of enterovirus infections is primarily directed to easing the symptoms (notably pain) and complications of the infection. U.S. Pat. No. 8,263,570 (to Ho et al) discusses treatment of EV-71 infection by inhibition of miR-141, a microRNA that provides post-transcriptional regulation of gene expression by RNA interference and that is upregulated in picornavirus infections. This inhibition is provided by an antisense oligonucleotide directed to miR-141 or and interfering RNA that targets EGR1. It should be appreciated, however, that miR-141 targets a wide variety of genes; as such the impact of such inhibition is unlikely to be specific for EV-71.

United States Patent Application Publication No. 2014/0023732 (to Cao et al) provides a combination of traditional Chinese medicines for the treatment of EV-71. These are provided as water or ethanol extracts prepared by soaking of various herbs, then mixed. Unfortunately no data is provided in regards to efficacy of such a combination, and due to variation in the starting materials it is unlikely that a given preparation is reproducible.

United States Patent Application No. 2016/0333075 (to Cardoa) describes the generation of specific monoclonal antibodies directed to EV-71 and, while focusing primarily on diagnostic uses, speculates that such antibodies of sufficiently high affinity could be useful for treatment. The application further describes the development of humanized antibodies having the desired specificity, but notes that such antibodies show tend to show reduced affinity. International Patent Application Publication No. WO 2008/148149 (to Rawlin et al) similarly describes passive immunization with polyclonal antibodies derived from eggs or colostrum as a method for treating EV-71 or preventing EV71 infection. Unfortunately wide ranging variation in the amount of virus present in different phases of infection makes determination of the appropriate dosage virus-directed antibodies dependent on accurate staging of the infection. This renders such virus-specific therapeutic antibodies a less than desirable compound for treating viral infection.

Despite many studies published on the pathogenesis of EV-A71 the mechanism of its progression to severe disease remains unclear. Several EV-A71 cellular receptors have been identified. However, their expression patterns cannot fully explain many aspects of this disease, including tissue tropism for viral replication and clinical manifestations.

Thus, there is still a need for a safe and effective means for treating and/or mitigating the effects of enterovirus infections.

SUMMARY OF THE INVENTION

The inventive subject matter provides compounds and methods that treat and/or prevent enteroviral infection (for example, by EV-A71) and/or their sequelae by reducing accessibility of the enterovirus to hWARS protein on the cell surface. In some embodiments this reduction in accessibility can be accomplished by reducing expression and/or transport of hWARS. In some embodiments this reduction in accessibility can be accomplished by occupancy of hWARS on the cell surface and/or occupancy of enteroviral hWARS receptors that reduce or eliminate interaction between hWARS and the enterovirus.

One embodiment of the inventive concept is a method of treating enteroviral (e.g. EV-A71) infection in an animal by introducing an hWARS blocking compound to the animal in an amount effective to at least partially block binding of the enterovirus to hWARS of the animal. The hWARS blocking compound can be an antibody, antibody fragment, or an antibody analog. Such an antibody can be a bispecific antibody having specificity for both hWARS and a co-receptor for the enterovirus (such as hSCARB2 and/or hPSGL1). The hWARS blocking compound can be a small molecule (i.e. having a molecular weight of less than or equal to 800 daltons). Such a small molecule can be used in combination with an antibody, antibody fragment, an antibody analog, or a bispecific antibody. The method can include prevention of infection of an animal with the enterovirus. The enterovirus can be EV-A71, or it can be an enterovirus other than EV-A71 (such as Coxsackie virus A16, Coxsackie virus A6, or Coxsackie virus A10). The method can include prevention or treatment of a sequelae of enterovirus infection, such as hand, foot, mouth disease, poliomyelitis, aseptic meningitis, pericarditis, or myocarditis. The method can include passive immunization, wherein the passive immunization provides blocking of a receptor for the enterovirus. The method can include administering a vaccine directed to the enterovirus that provides an active immunization.

Another embodiment of the inventive concept is a method of treating infection of an animal by an enterovirus (such as EV-A71) that includes introducing a soluble hWARS or a soluble hWARS analog to the animal in an amount effective to at least partially occupy an hWARS receptor of the enterovirus. In such an embodiment the soluble hWARS or the soluble hWARS analog can be an hWARS protein, an hWARS peptide, a chemically modified hWARS protein, a chemically modified hWARS peptide, and/or a small (i.e. having a molecular weight of less than or equal to 800 daltons) molecule analog of hWARS. A chemically modified hWARS protein or chemically modified hWARS peptide can be modified by PEGylation. Such a method can prevent infection of an animal with the enterovirus. The enterovirus can be EV-A71. Alternatively, the enterovirus can be an enterovirus other than EV-A71 (such as Coxsackie virus A16, Coxsackie virus A6, and/or Coxsackie virus A1019). The method of treatment include prevention or treatment of a sequelae of enterovirus infection, such as hand, foot, mouth disease, poliomyelitis, aseptic meningitis, pericarditis, and/or myocarditis. In such methods the soluble hWARS or hWARS analog can be co-administered with an hWARS blocking compound. Similarly, such methods can be used in conjunction with the administration of a vaccine directed to the enterovirus.

Another embodiment of the inventive concept is a method of treating infection of an animal by an enterovirus (such as EV-A71) that includes introducing an inhibitor of a pro-inflammatory peptide (such as IFNγ) function to the animal in an amount that is effective to at least partially reduce expression or translocation of hWARS. The inhibition can include reducing expression of the pro-inflammatory peptide, reducing release of the pro-inflammatory peptide, reducing activity of the pro-inflammatory peptide, and/or reducing the activity of a secondary messenger associated with the pro-inflammatory peptide. The inhibitor can be administered in conjunction with soluble hWARS, a soluble hWARS analog, and/or an hWARS blocking compound. The method can used in conjunction with the administration of a vaccine directed to the enterovirus.

Another embodiment of the inventive concept is a method of treating infection of an animal by an enterovirus (such as EV-A71) that includes modifying an existing balance between T-helper1 and T-helper2 activity in the animal. This balance can be modified by altering (for example, reducing) the activity of a pro-inflammatory peptide, such as IFNγ. Such activity can be reduced by reducing expression of the pro-inflammatory peptide and/or reducing release of the pro-inflammatory peptide. Similarly, the alteration in activity can be a reduction in the activity of a secondary messenger associated with the pro-inflammatory peptide.

Another embodiment of the inventive concept is the use of an hWARS blocking compound in preparing a medicament useful in treating infection of an animal by an enterovirus (such as EV-A71), where the medicament includes an hWARS blocking compound in an amount that is effective to at least partially block binding of the enterovirus to hWARS. Such a blocking compound can be an antibody, antibody fragment, an antibody analog, and/or a small molecule (i.e. a molecule having a molecular weight of less than or equal to 800 daltons). The antibody can be a bispecific antibody having specificity for both hWARS and a co-receptor (such as hSCARB2 and hPSGL1) for the enterovirus. Such a medicament can be useful in preventing infection of an animal with an enterovirus. The enterovirus can be EV-A71. Alternatively, the enterovirus can be an enterovirus other than EV-A71, such a Coxsackie virus A16, Coxsackie virus A6, and/or Coxsackie virus A10. The medicament can be useful in preventing or treating sequelae of enterovirus infection, such as hand, foot, mouth disease, poliomyelitis, aseptic meningitis, pericarditis, and myocarditis. The medicament can provide a passive immunization (such as blocking a receptor for the enterovirus), and can include a vaccine directed towards the enterovirus that provides an active immunization.

Another embodiment of the inventive concept is the use of a soluble hWARS and/or a soluble hWARS analog to prepare a medicament useful in treating infection of an animal by an enterovirus (such as EV-A71), where the medicament includes the soluble hWARS and/or soluble hWARS analog in an amount effective to at least partially occupy an hWARS receptor of the enterovirus. The soluble hWARS and/or soluble hWARS analog can be an hWARS protein, an hWARS peptide, a chemically modified hWARS protein, a chemically modified hWARS peptide, and/or a small molecule (i.e. having a molecular mass of less than or equal to 800 daltons) analog of hWARS. The chemically modified hWARS protein or chemically modified hWARS peptide can be PEGylated. The enterovirus can be EV-A71 or, alternatively, an enterovirus other than EV-A71 (such as Coxsackie virus A16, Coxsackie virus A6, and/or Coxsackie virus A1019). The medicament can be useful in preventing infection of an animal with the enterovirus. The medicament can be useful in preventing and/or treating sequelae of enterovirus infection, such as hand, foot, mouth disease, poliomyelitis, aseptic meningitis, pericarditis, and/or myocarditis. The medicament can include an hWARS blocking compound and/or a vaccine directed to the enterovirus.

Another embodiment of the inventive concept is the use of an inhibitor of a pro-inflammatory peptide (such as IFNγ) function in preparing a medicament useful for treating infection of an animal by an enterovirus (such as EV-A71), where the medicament includes the inhibitor of the pro-inflammatory peptide function in an amount effective to at least partially reduce expression or translocation of hWARS in the animal. Pro-inflammatory peptide function can be reduced by reducing expression of the pro-inflammatory peptide, reducing release of the pro-inflammatory peptide, reducing activity of the pro-inflammatory peptide, and/or reducing activity of a secondary messenger associated with the pro-inflammatory peptide. The medicament can include a soluble hWARS, a soluble hWARS analog, an hWARS blocking compound, and/or a vaccine directed to the enterovirus.

Various objects, features, aspects and advantages of the inventive subject matter will become more apparent from the following detailed description of preferred embodiments.

BRIEF DESCRIPTION OF THE DRAWINGS

FIGS. 1A to 1G show data demonstrating a requirement for hWARS activity for EV-A71 infection. FIG. 1A depicts generation of a hWARS knockdown (hWARS KD) cell line. RD cells were stably transfected with shRNA targeting hWARS. The amount of hWARS mRNA was characterized. RD cells transfected with a control shRNA (control RD) are included for comparison. The hWARS KD cells and control RD cells were subsequently challenged with EV-A71. FIG. 1B shows the copy numbers of EV-A71 RNAs found in infected hWARS KD cells and control RD cell. FIG. 1C provides photomicrographs of cells immunostained to show EV-A71 proteins, performed using anti-EV-A71 antibodies. FIG. 1D shows typical results of Western blot analyses performed to detect EV-A71 protein in control RD (lane 1) and hWARS KD cells (lane 2) one day after EV-A71 inoculation. Endogenous γ-tubulin was utilized as a loading control. FIG. 1E shows viral RNA genome copy number from EV-A71, measured after hWARS KD cells were transfected with hWARS cDNA (lane 1) or an empty vector (lane 2) and followed by challenge with EV-A71. FIG. 1F shows differential cytopathic effects of enterovirus serotypes in hWARS KD and control RD cells. The percentages (%) of cytopathic effects of the same virus in hWARS KD and in control RD cells were examined on the same day.

FIG. 1G shows typical results from characterization of viral loads produced by control RD cells relative to hWARS KD cells. The known enterovirus receptors for individual serotypes are depicted as follows: "+" indicates receptor usage; "−" indicates receptor not been used; "n.r." indicates receptor not been reported; EV for enterovirus A; CV-A for coxsackievirus A; E for echovirus; CV-B for coxsackievirus B; PV for poliovirus; EV-D for enterovirus D. CAR for coxsackievirus and adenovirus receptor. Error bars represent the mean±s.d. of three independent experiments. Asterisks indicate significant differences with p<0.05. Asterisks with brackets (*) indicate significant differences with p<0.05 where the cytopathic effect and the viral load produced in hWARS KD cells were more prominent compared to those of control RD cells. Images shown are representative of three independent experiments.

FIGS. 2A to 2H show the impact of hWARS on early EV-A71 replication. FIG. 2A shows the amount of EV-A71 RNA in hWARS-knockdown (KD) RD cells (black line) and control RD (gray line) cells during early infection. FIG. 2B provides photomicrographs of immunostaining for EV-A71 protein in hWARS-KD cells transfected with control RNA (left), hWARS-KD cells transfected with purified EV-A71 RNA (middle), and control RD cells transfected with EV-A71 RNA (right). FIG. 2C shows the results of confocal microscopy for endogenous hWARS expression. RD cells are shown following staining with anti-hWARS antibodies (left panel); a corresponding bright field image is shown in the middle panel. An overlapping image of the hWARS protein and the bright field (middle) is in provided in the right panel. Arrows indicate positively staining for hWARS. FIG. 2D shows results of an attachment assay for EV-A71 to hWARS, hSCARB2 and hPSGL 1. High-titer EV-A71 was incubated with non-permissive L929 cells overexpressing hWARS, hSCARB2 and hPSGL 1, separately, at 4° C. for 2 hours, then washed to remove unbound viruses before fixation for immunostaining directed to EV-A71 (left panel) and hWARS, hSCARB2 or hPSGL 1 (middle panel). The degree of co-localization of EV-A71 and hWARS, hSCARB2 or hPSGL 1 (right panel) was estimated using Mander's Original co-localization coefficient (R). FIG. 2E shows typical results of Western blot analyses of EV-A71 protein in L929 cells transfected with a control vector (lane 1), irrelevant cDNA (lane 2), hWARS-cDNA (lane 3), hSCARB2-cDNA (lane 5) or hPSGL 1-cDNA (lane 6). Mock-transfected L929 (negative control, lane 4) and EV-A71-infected RD cells (positive control, lane 7) are also shown. FIG. 2F shows results of pull-down studies directed to EV-A71 by recombinant hWARS protein. Recombinant hWARS protein was coupled to agarose before inoculation with three different clinical EV-A71 isolates for overnight at 4° C. After washing away unbound viruses, complexes were dissociated for Western blot analyses using anti-EV-A71 antibodies. FIG. 2G shows the results of anti-hWARS antibodies blockage of EV-A71 infection. Surface hWARS of RD cells were blocked with anti-hWARS antibodies for 1 hour prior to EV-A71 infection. Virus production ($TCID_{50}$) in conditioned supernatants (top panel) and viral protein expression in infected cell lysates (bottom panel) are shown. FIG. 2H shows saturation of EV-A71 virions by recombinant hWARS protein. EV-A71 was pre-incubated with recombinant hWARS protein prior to challenge of RD cells. Virus production (top panel) and viral protein expression (bottom panel) were measured as described for FIG. 2G. "r" represents the Pearson's correlation coefficient. Error bars in a, g and h represent the mean±s.d. of three independent experiments. Images shown in b, c, d, e, f, g and h are representatives of three independent experiments.

FIG. 3A shows IFNγ induced hWARS, but not hSCARB2 or hPSGL 1 expression. Different doses of IFNγ (0, 10, 50 and 100 U/ml) were administrated to NT2 (left panels) and RD (right panels) cells for 48 hours followed by EV-A71 infection. Quantitative reverse transcription polymerase chain reaction (qPCR; top panels) and Western blot (bottom panels) analyses were performed to detect the mRNA expression levels of hWARS (dark), hSCARB2 (grey) and hPSGL 1 (dark grey), respectively. EV-A71 infections were confirmed by Western blot analyses using anti-EV-A71 antibodies. Endogenous glyceraldehyde 3-phosphate dehydrogenase (GAPDH) and γ-tubulin were detected as loading controls for the qPCR and Western blot analyses, respectively. FIG. 3B shows induced expression and plasma membrane translocation of hWARS after treating with IFNγ. NT2 (left panel) and RD (right panel) cells were treated with 100 U/ml IFNγ ("+") or mock-treated ("−") for 72 hrs followed by subcellular fractionation. The hWARS protein expression in the cytoplasm and plasma membrane fractions was characterized using anti-hWARS antibodies. Total crude extracts were included as controls. Enrichment of cytosolic protein GAPDH in the cytoplasmic fractions and enrichment of plasma membrane protein sodium potassium ATPase (Na+/K+-ATPase) in the plasma membrane fractions were confirmed by immunoblotting using specific antibodies. Images shown are representatives of three independent experiments. Asterisks indicate non-specific bands.

FIG. 4A shows typical results of Western blot analyses of EV-A71 protein in EV-A71-challenged neonatal BALB/c mice pre-transduced with empty lentiviral vector (lanes 2 and 3) showing little or mild EV-A71 infection, or lentiviral vector expressing hWARS (lanes 4 and 5) showing positive EV-A71 infection. Two randomly chosen samples were included in each category. Mice transduced with empty lentiviral vector only (lane 1) and EV-A71-infected RD cells (lane 6) were analyzed as controls. FIG. 4B provides representative images of muscle fibers from the hWARS-transduced mice. Tissues of EV-A71-infected mice were immunostained with anti-EV-A71 (left panels) and anti-hWARS antibodies (middle panels), respectively. Tissues of empty lentiviral vector-transduced mice inoculated with PBS served as a negative control (bottom panels). The OAP I-stained nuclei are also shown in the merged images (right panels). FIG. 4C provides representative images of cells from the brains of the infected (top panels) and uninfected (bottom panels) mice subjected to immunofluorescent staining, with anti-EV-471 antibodies (left panels) or anti-hWARS antibodies (middle panels). Merged images are provided in the right panels. FIG. 1D shows the results of histopathology studies of EV-A71-inoculated hWARS-transduced mice. Interstitial infiltration of lymphocytes in various organs were detected using anti-CD 19 antibodies (light gray, left panels). The nuclei were stained with DAPI (dark gray). Hematoxylin and eosin stain showed inflammatory infiltrates of mononuclear cells (arrow heads) and degenerated neuronal cells (arrows) in right panels. Images shown were chosen from three independent experiments.

DETAILED DESCRIPTION

Figure 1A:
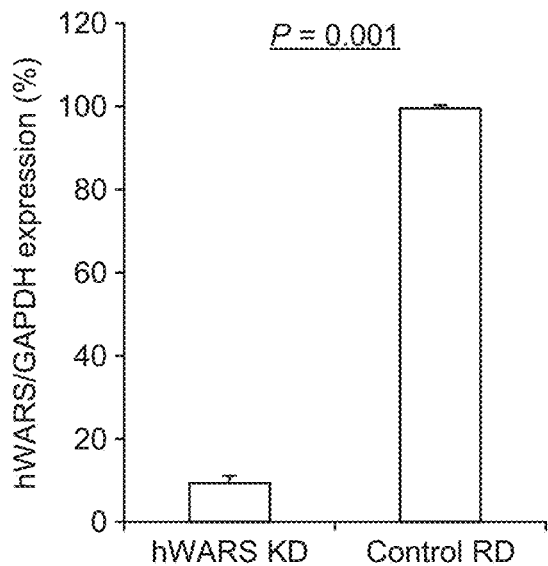

The following description includes information that can be useful in understanding the present invention. It is not an admission that any of the information provided herein is prior art or relevant to the presently claimed invention, or that any publication specifically or implicitly referenced is prior art.

The inventive subject matter provides apparatus, systems and methods in which the finding that tryptophanyl-tRNA synthetase (WARS) can be identified as a cellular surface receptor for enteroviruses, including enterovirus 71 (EV-A71), is utilized in the treatment of EV-71 infection and in the generation of cell culture and animal models for human EV-A71 infection. Compositions and methods that reduce the expression of WARS and/or translocation of WARS to the cell surface, for example by reducing induction by gamma interferon, can reduce entry of EV-A71 into susceptible cells. Similarly, compositions and methods that block WARS at the cell surface (for example, though the use of specific antibodies and/or antibody fragments) can reduce entry of EV-A71 into susceptible cells. Such compositions and methods can be useful in the treatment and prevention of infection by EV-A7 land other enteroviruses. Similarly, induction of the expression of WARS in animals and cultured cells can render such animals and cells susceptible to EV-A71 infection, thereby providing non-human models of human disease. Such animal models and cultured cell models can be utilized in the development of treatment and/or preventative modalities, in addition to aiding in the development of diagnostic tools.

Various objects, features, aspects and advantages of the inventive subject matter will become more apparent from the following detailed description of preferred embodiments, along with the accompanying drawing figures in which like numerals represent like components.

One should appreciate that the disclosed techniques provide many advantageous technical effects including safe and effective treatment and/or prevention of enterovirus infections.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Previously, WARS has not been known to act as a viral receptor and has therefore not been utilized as a therapeutic or diagnostic target for enteroviral (EV) infection. Inventors identified WARS as a viral receptor for a variety of EV serotypes following performance of a short-hairpin RNA (shRNA) lentiviral library screening for human genome transcripts that are required for EV-A71 replication. Since direct lentiviral transduction can trigger an inflammatory response, such a screening approach can facilitate the identification of novel immune-inducible cellular factors that are critical for EV-A71 replication.

In a typical study a lentiviral shRNA library targeting 54,509 human transcripts was transduced into $3 \times 10^8$ rhabdomyosarcoma (RD) cells, which are highly susceptible to EV-A71 infection. RD cells carrying individual discrete shRNAs were challenged using a high titer of EV-A71. Without wishing to be bound by theory, the inventors theorize that knockdown of a cellular gene that is critical for EV-A71 replication would halt the virus replication and hence protect the cells from EV-A71-induced cytopathic effect (CPE). Total RNAs from the pool of EV-A71 resistant cells were isolated and the associated shRNAs were identified using an Affymetrix microarray. Inventors identified 118 candidate genes, the knockdown of which protected RD cells from EV-A71-induced CPE (see NCBI's Gene Expression Omnibus (GEO) Database via GEO accession number: GSE80407). Candidate genes were selected for validation based on their expression levels and the number of unique shRNAs targeting the same gene. Without wishing to be bound by theory, Inventors anticipate that knockdown of highly expressed genes could have a more pronounced effect on EV-A71 replication, and that knockdown by multiple unique shRNAs would prevent off-targeting. Filtering by these criteria led to a candidate human gene named hWARS, silencing of which effectively protected RD cells from EV-A71-induced CPE.

Figure 1B:
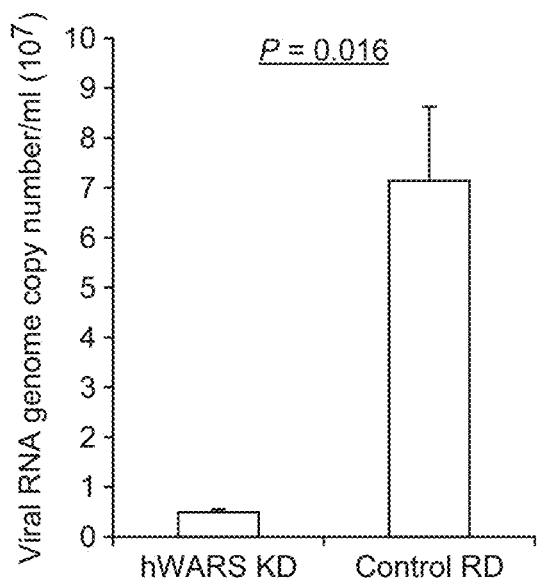
Figure 1C:
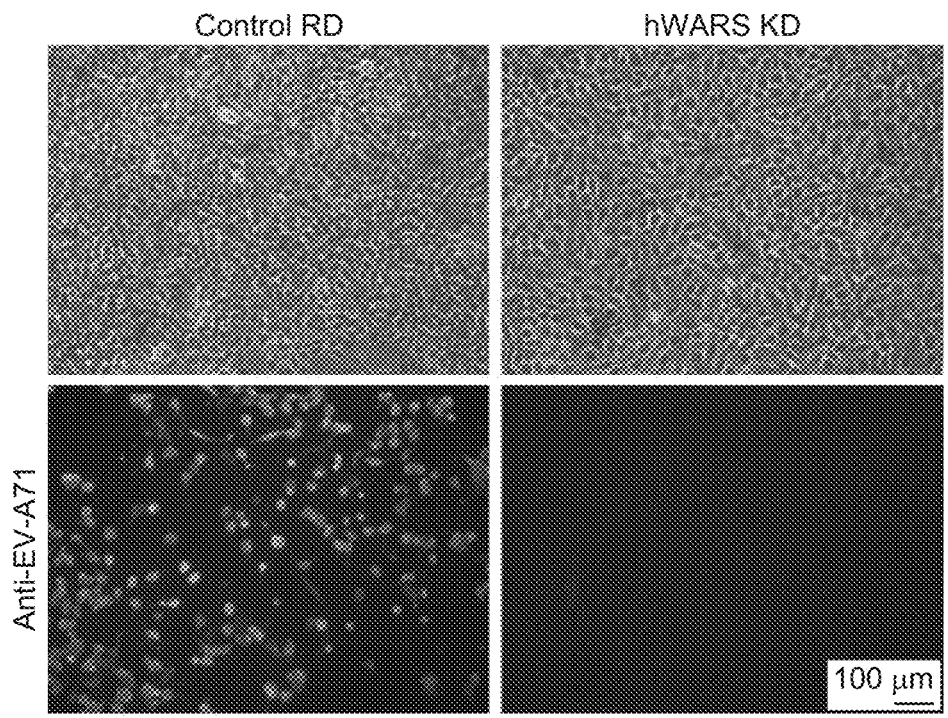
Figure 1D:
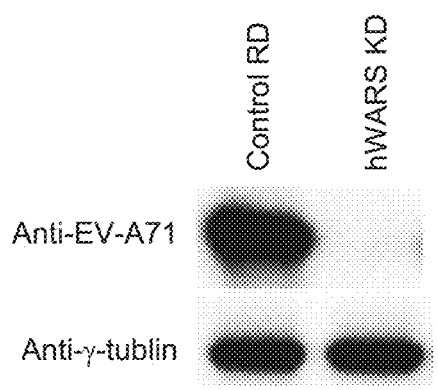
Figure 1E:
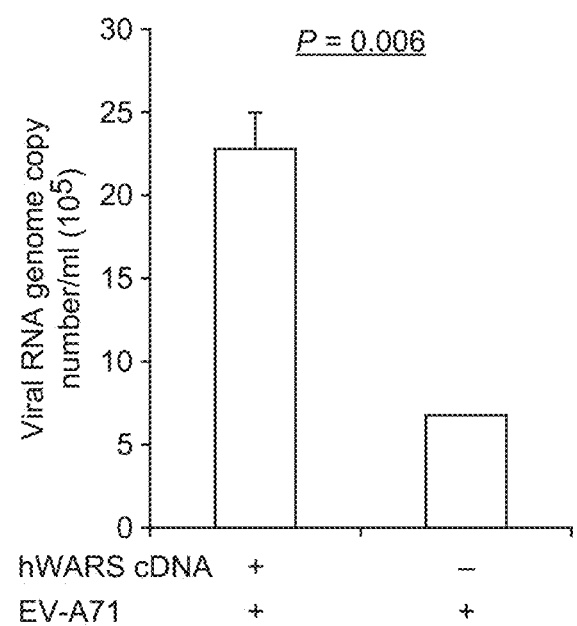

To establish the importance of hWARS in EV-A71 replication, an independent RD cell clone stably expressing two hWARS shRNAs that were identified in the shRNA lentiviral library screening was generated (see FIG. 1A). These sequences can be found in the NCBI's Gene Expression Omnibus (GEO) database via the GEO accession number: GSE80407. The first siRNA sequence targets the gene encoding Human tryptophanyl-tRNA synthetase (WRS), herein referred to as shWARS1: 5'-GGACGACGACAAGCTCGAGCAGATCAG-3' (SEQ ID NO:13). The second siRNA sequence targets the gene encoding *Homo sapiens* tryptophanyl-tRNA synthetase (WARS), mRNA, herein referred to as shWARS2: 5'-CCAGACCATGCATGTAGTCCACTCCAG-3' (SEQ ID NO:14). This clone was consistently found to be highly resistant to EV-A71 infection (see FIGS. 1B, 1C, and 1D). Replenishment of hWARS by transfecting such cells with a hWARS hyperexpression plasmid can partially restore their susceptibility to EV-A71 (see FIG. 1E). Thus, the loss-of-function and gain of function experiments consistently supported the finding that hWARS is essential for productive EV-A71 replication.

In addition to EV-A71 there are many other serotypes of enteroviruses, which can cause a myriad of diseases ranging from self-limiting febrile exanthematous illness to fatal visceral involvement. Most Enterovirus A serotypes such as A6, A8, A10 and A16 are known to cause HFMD, herpangina, aseptic meningitis and acute flaccid paralysis. Enterovirus B serotypes such as Echovirus 6, 11, 25, 30 and Coxsackie B2 and B5 are especially known to cause infantile liver failure, myocarditis, pericarditis, pneumonia, encephalitis, and sudden or cot death. A major 2014 US outbreak of Enterovirus D68 was associated with severe respiratory illness and fatal acute flaccid myelitis. It should be appreciated that different cellular receptor for host cell entry can be used by different serotypes of enteroviruses within the same species group.

Figure 1F:
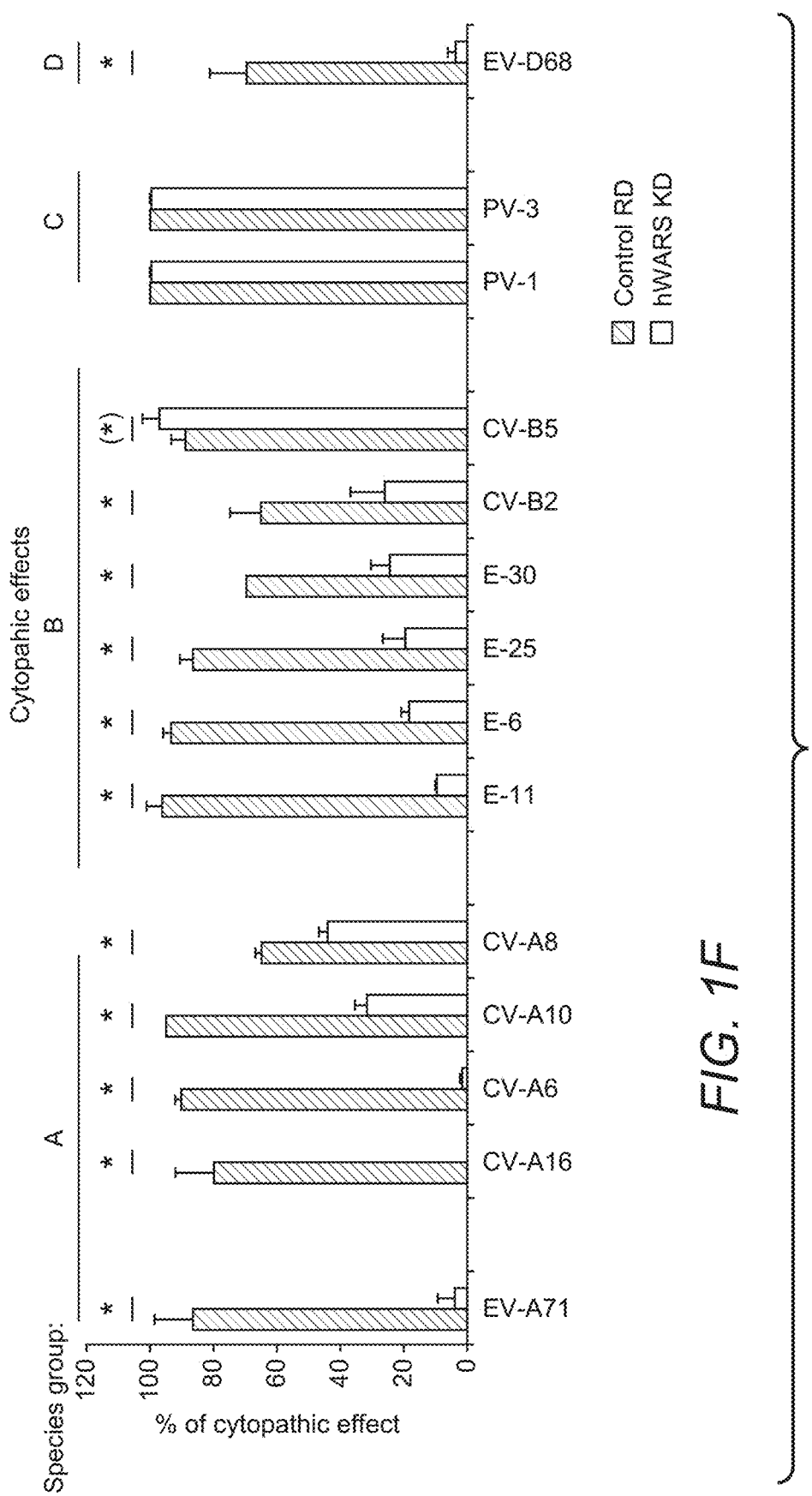

The requirement of hWARS in RD cells for viral replication by the aforementioned common human enterovirus isolates of different serotypes was tested. Surprisingly Inventors found that a broad spectrum of protection from attack by different serotypes of enterovirus species is provided to RD cells when the expression of hWARS is reduced. This is shown by a decrease in the cytopathic effects and the viral loads of the challenged hWARS knockdown RD cells when compared with those of the controls. Exceptions included Coxsackie virus B5 and the polioviruses, which are known to utilize other host proteins as receptors (as shown in FIGS. 1F and 1G).

Figure 2A:
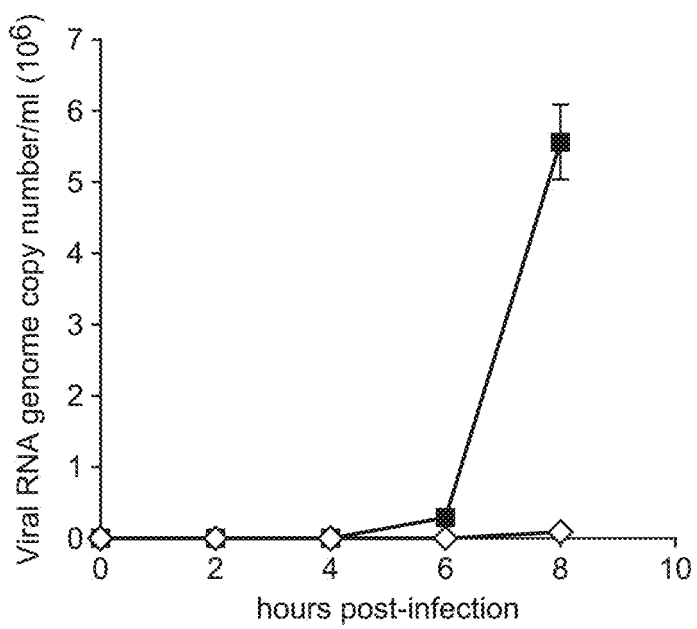

Although hWARS was initially identified as an aminoacyl-tRNA synthetase catalyzing the attachment of tryptophan onto cognate tRNA, additional roles in angiogenesis, cytoskeletal reorganization and shear stress-responsive gene expression have also been suggested. Its function as an enterovirus receptor protein, however, has not been previously known. EV-A71 has a positive-stranded RNA genome that can serve as template for the synthesis of both viral proteins and RNAs. Inventors reasoned that both processes would be affected if hWARS was a key functional element at an early stage of the infection process (e.g. prior to the bifurcation of viral RNA replication and viral protein synthesis). Both viral proteins and viral RNAs were found to be significantly reduced in hWARS-knockdown RD cells (FIGS. 1B, 1C and 1G), indicating that a hWARS is involved in a early stage of the EV-A71 infective process. Consistent with known EV-A71 replication kinetics, an increase in viral RNA production was noted as early as 4 hours post-infection in infected RD cells. This phenomena, however, was completely abrogated in hWARS knockdown cells (see FIG. 2A). These results further support finding that hWARS provides a key function of an early stage of EV-A71 infection, possibly before or at the start of viral RNA synthesis.

Figure 2B:
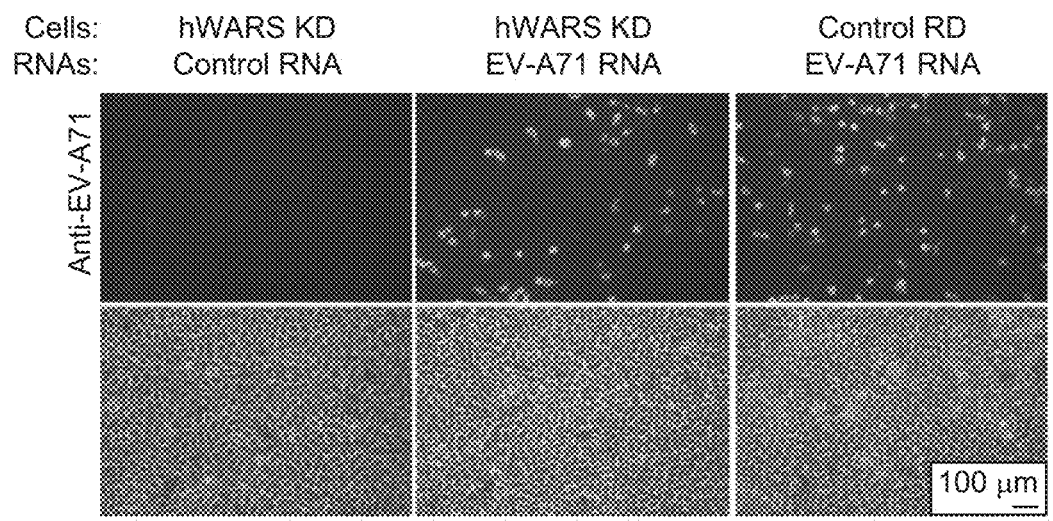

To identify the point of interaction between EV-A71 and hWARS, Inventors transfected purified EV-A71 RNAs into hWARS knockdown RD cells and into control cells. Detection of similar levels of viral protein expression in both cell lines indicated that the downstream machineries of EV-A71 replication remain intact in hWARS deficient RD cells (FIG. 2B). These results indicate that hWARS has a previously unknown and essential role during the step of viral entry into the cell.

Figure 2C:
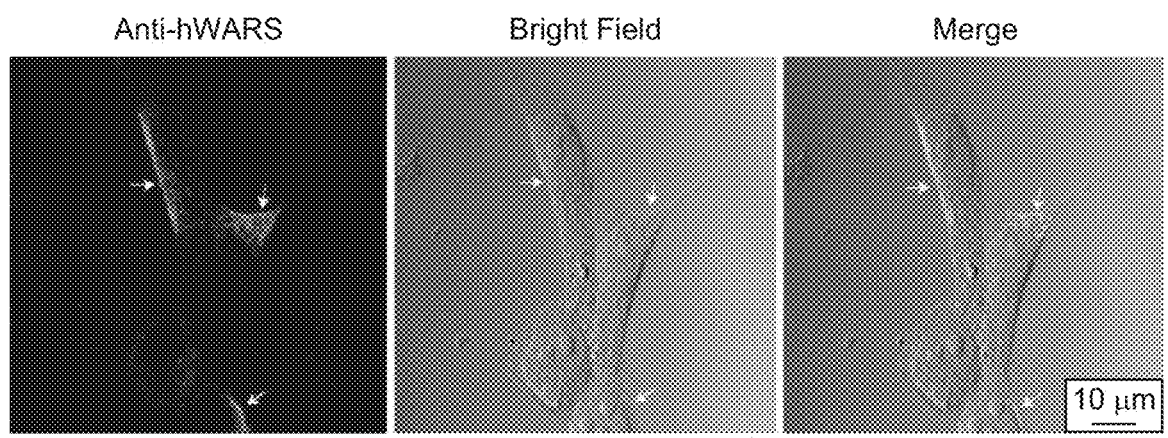

Inventors hypothesized that if hWARS is essential for EV-A71 entry the gene product should reside (at least partially) on the cell surface. To determine the surface expression of endogenous hWARS, Inventors stained RD cells with anti-hWARS antibodies under non-permeabilized conditions and observed a sharp and polarized spindle-like pattern of hWARS concentrated at the cell periphery (FIG. 2C) using confocal microscopy. The membrane association of hWARS was further revealed in the orthogonal view of the anti-hWARS-stained RD cells treated with 0.1% triton X-100.

Figure 2D:
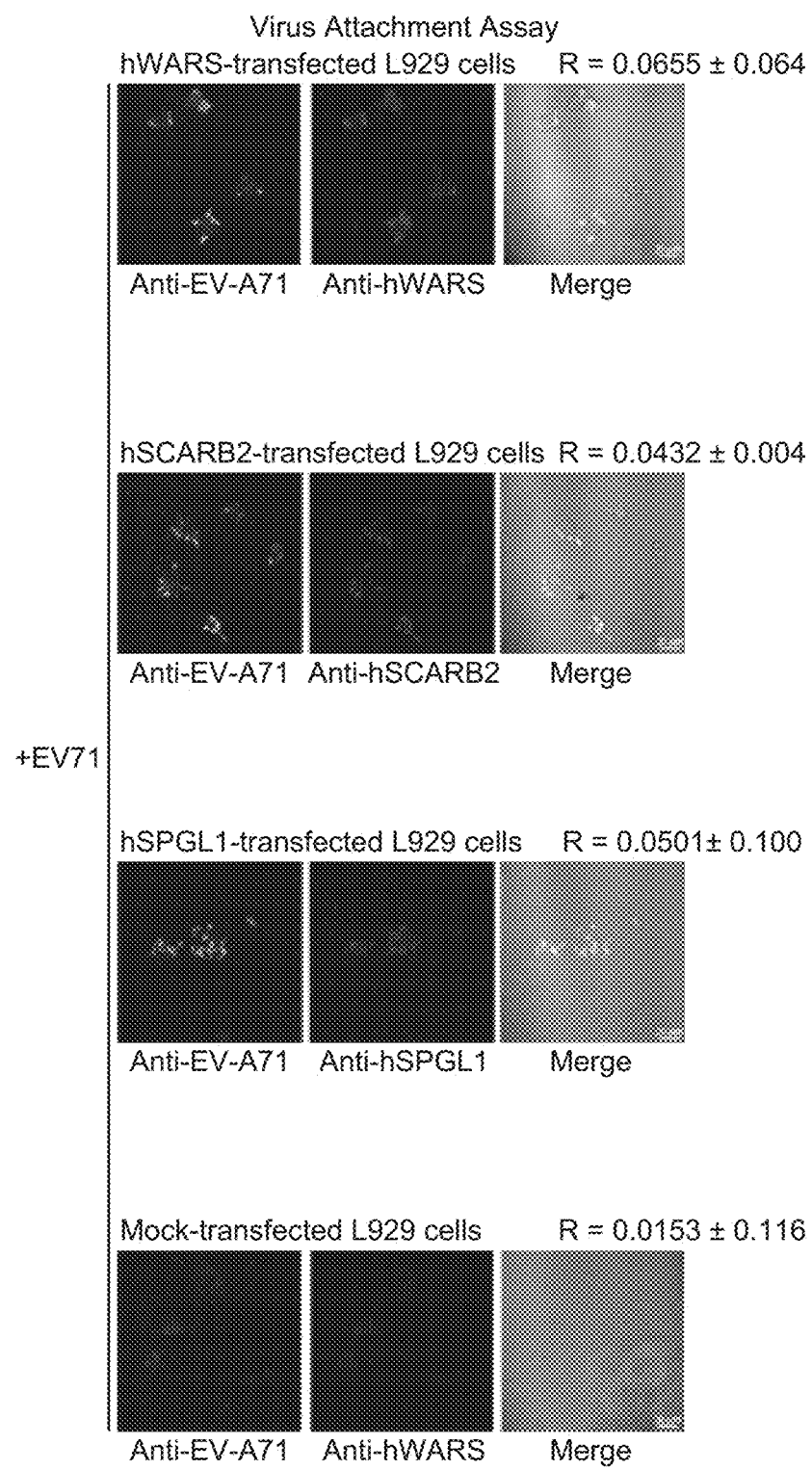
Figure 2E:
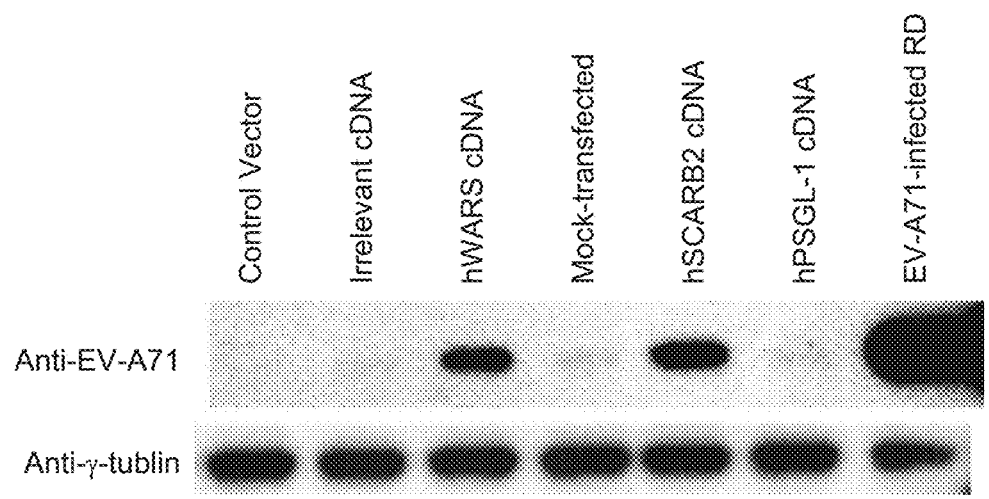

Though many cellular factors have been identified that modulate the efficiency of EV-A71 entry, EV-A71 pathogenesis has generally been attributed to the tissue expression patterns of two known cellular receptors: human scavenger receptor class B member 2 (hSCARB2) and human P-selectin glycoprotein ligand-1 (hPSGL1). Functional comparative studies of hSCARB2 and hPSGL1, however, revealed major discrepancies between their virus binding capacities and infection efficiencies. Virus attachment assays in a non-permissive mouse cell line (L929) expressing EV-A71 receptors detected a higher degree of co-localization of EV-A71 to hPSGL1-transfected L929 cells [co-localization coefficient (R)=0.501±0.100] than to hSCARB2-transfected L929 cells (R=0.432±0.004) (FIG. 2D). Surprisingly, L929 cells expressing hWARS showed the highest binding capacity for EV-A71 (R=0.655±0.064). Inventors also compared the EV-A71 infection efficiency in L929 cells expressing hWARS, hSCARB2, and hPSGL1. Similar levels of viral protein were detected in cell lysates harvested from the EV-A71-inoculated L929 cells expressing either hWARS or hSCARB2 suggesting that both surface proteins can effectively sensitize cells that are normally non-permissive to EV-A71 infection (FIG. 2E). Such cell lines can be established for the characterization of enterovirus infection, screening of potential anti-enterovirus compounds, and development of diagnostic tools through modification of the cells to express hWARS. Minimal to no EV-A71 viral protein were detected in cell lysates harvested from L929 cells expressing hPSGL1.

Figure 2F:
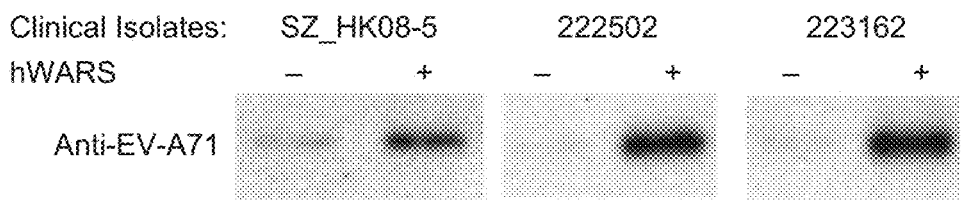

Direct interaction between the hWARS and EV-A71 was further confirmed by in vitro pull-down experiments. Three EV-A71 clinical isolates were chosen to test their binding capacities to resin beads coupled with immune complexes containing the hWARS protein and anti-hWARS antibodies. The results from such in vitro pull-down assays showed that all tested clinical isolates were highly enriched in an immune complex containing both hWARS protein and anti-hWARS antibodies, but they did not bind to anti-hWARS antibodies alone (FIG. 2F).

The functional importance of hWARS for EV-A71 host entry was further demonstrated by antibody blocking of hWARS at the cell surface. Various amount of anti-hWARS antibodies were administrated to RD cells prior to EV-A71 infection. A dose-dependent reduction of the viral loads and the viral proteins were seen in cells treated with progressively increasing concentrations of anti-hWARS antibodies, showing that the anti-hWARS antibodies can hinder EV-A71 infection (FIG. 2G). Such antibodies, related antibody fragments (e.g. Fab, F(ab)$_2$, Fab', Fv, etc.), and/or antibody analogs (e.g. single chain antibodies, humanized antibodies, etc.) can, therefore, be utilized in the treatment and/or prevention of infection by EV-A71 and other enterovirus serotypes.

Such antibodies, antibody fragments, and/or antibody can be provided as an intravenous infusion, for example as a solution or suspension in a saline solution. Alternatively, hWARS-specific antibodies, antibody fragments, and/or antibody analogs can be provided in lyophilized or dried form that is reconstituted prior to use. For treatment or prevention of EV-A71 (or other suitable enterovirus serotype) infection anti-hWARS antibody, antibody fragment, and/or antibody analog can be supplied at from 10 pig/kg to 10 mg/kg body weight. In some embodiments a single infusion of antibody, antibody fragment, and/or antibody analog can be effective. In other embodiments repeated or continuous infusion can be used. Repeated infusions can be applied at intervals ranging from 3 times a day to once a week.

In some embodiments hWARS-specific antibodies, antibody fragments, and/or antibody analogs can be provided in combination with one or more anti-viral and/or anti-inflammatory compounds. Such anti-viral and/or anti-inflammatory compounds can be included with an hWARS-specific antibody, antibody fragment, and/or antibody analog containing composition, or can be co-administered. If co-administered the anti-viral and/or anti-inflammatory compounds can be provided on the same schedule as the hWARS-specific antibody, antibody fragment, and/or antibody analog composition, or on a different schedule.

Similarly, saturating the surface antigens of EV-A71 by pre-incubating the viruses with the soluble recombinant hWARS protein prior to infection showed an a reduction in infectivity as the viruses were pre-treated with increasing amount of soluble recombinant hWARS protein (FIG. 2H). This suggests that hWARS proteins, peptides, and/or analogs thereof (for example, PEGylated derivatives) can be used to treat and/or prevent enterovirus infections.

Such hWARS proteins, peptides, and/or analogs can be provided as an intravenous infusion, for example as a solution or suspension in a saline solution. Alternatively, hWARS proteins, peptides, and/or analogs can be provided in lyophilized or dried form that is reconstituted prior to use. For treatment or prevention of EV-A71 (or other suitable enterovirus serotype) infection hWARS proteins, peptides, and/or analogs can be supplied at from 10 µg/kg to 10 mg/kg body weight. In some embodiments a single infusion of hWARS proteins, peptides, and/or analogs can be effective. In other embodiments repeated or continuous infusion can be used. Repeated infusions can be applied at intervals ranging from 3 times a day to once a week.

In some embodiments hWARS proteins, peptides, and/or analogs can be provided in combination with one or more anti-viral and/or anti-inflammatory compounds. Such anti-viral and/or anti-inflammatory compounds can be included with an hWARS proteins, peptides, and/or analogs containing composition, or can be co-administered. If co-administered the anti-viral and/or anti-inflammatory compounds can be provided on the same schedule as the hWARS proteins, peptides, and/or analogs composition, or on a different schedule.

Overall, the inventors have found that hWARS represents a novel EV-A71 cellular receptor that provides opportunities for treatment modalities that can reduce or eliminate enterovirus infections, for example by reducing expression of hWARS, blocking hWARS at the cell surface (for example, with specific antibodies, antibody fragments, and/or antibody analogs), and/or saturating viral binding sites with hWARS protein, peptides, and/or analogs (for example, small molecule analogs). It is known that EV-A71 can enter host cells using different cellular receptors. Due to the relatively robust expression of hSCARB2 in lysosomes and endosomes of many cell types, hSCARB2 has been proposed to be the major receptor for systemic EV-A71 infection. Its expression pattern, however, cannot fully explain clinical complications, especially in the cases of severe EV-A71 infection. The identification of hPSGL1, a leukocyte-specific membrane protein as an alternative receptor for EV-A71 infection has been proposed for the infiltration of EV-A71-infected leukocyte into the central nervous system which accounts for the neurotropism of EV-A71. However, the absolute requirement of hPSGL1 for EV-A71 cell entry remains elusive as not all tested EV-A71 strains can utilize this receptor for infection. It remains unclear which cellular receptor plays a key role in EV-A71 neurotropism.

Figure 3A:
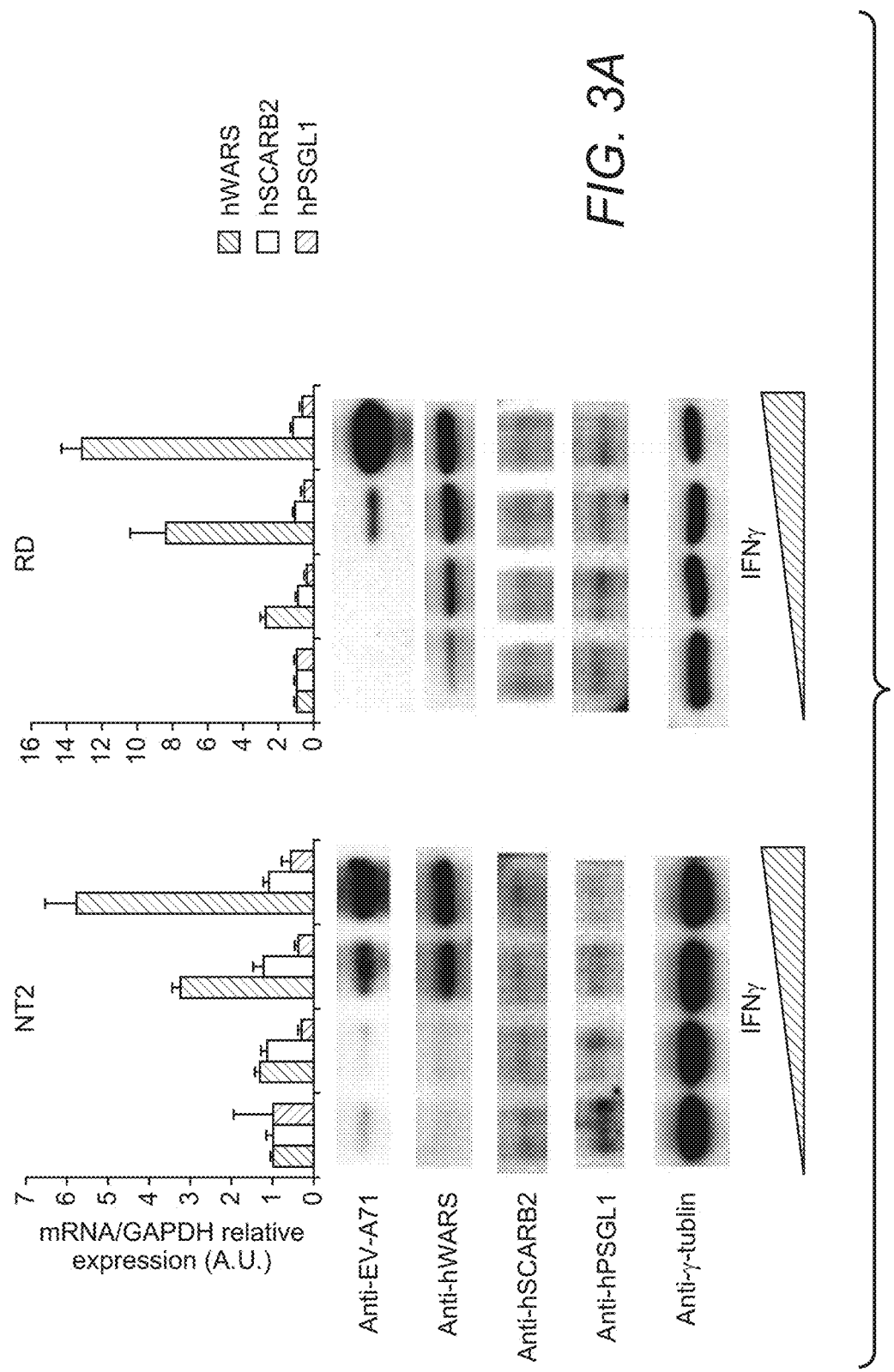
FIGS. 3A and 3B show results of hWARS sensitization of cells that are normally non-permissive to EV-A71 infection.
Figure 3B:
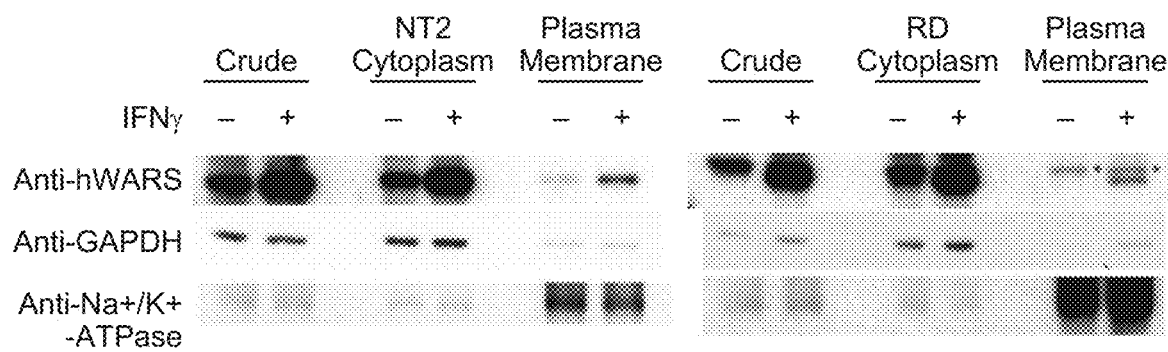

Surprisingly, Inventors have also found that hWARS expression can respond to external stimulation by IFNγ (FIG. 3A). Since cytokine response is a common mechanism for anti-viral defense, without wishing to be bound by theory Inventors believe that certain cell types can become sensitized to EV-A71 infection following such a host-mounted innate immune response to primary infection. This was tested using a human teratocarcinoma cell line, NT2, which exhibits properties of a committed neuronal precursor at an early stage of development. Under low-titer infection conditions, NT2 can only moderately support EV-A71 replication (FIG. 3A, lane 1; left). IFNγ was then added to the culture media to mimic the cytokine production that can occur upon primary infection. Using specific antibodies and primers for Western blot and quantitative reverse transcription polymerase chain reaction (qPCR) analyses, respectively, the inventors identified an enhanced expression of hWARS (but not hSCARB2 or hPSGL1) in cells treated with IFNγ, in a dose-dependent manner (FIGS. 3A and 3C). Surprisingly, plasma membrane translocation of hWARS was also observed upon IFNγ stimulation (FIG. 3B). This is consistent with an infection model where hWARS can act as an IFNγ-inducible cellular receptor for EV-A71 infection.

This suggests that therapies that reduce the production, release, and/or function of IFNγ can be useful in the treatment and/or prevention of enterovirus infections. This also suggests that therapies that reduce the production, release, and/or function of IFNγ can reduce or eliminate the occurrence of neurological sequelae of enterovirus infection. Similarly, the inventors contemplate that reducing the activity of secondary messengers of such pro-inflammatory peptides can similarly provide treatment for enteroviral infections, and/or reduce neurological sequelae of such infections.

In some embodiments of the inventive concept such IFNγ inhibition can be provided by the administration of an antibody, antibody fragment, and/or antibody analog specific for IFNγ. In other embodiments the functions of IFNγ can be inhibited, for example by administration of glucocorticoids (such as dexamethasone), short chain fatty acids (such as butyrate), and certain proteins (such as CC16). Inventors contemplate that administration of such proteins and/or compounds can provide an effective therapeutic mode for treatment of infection by enteroviruses (such as EV-A71) and/or their sequelae. Such proteins or compounds can be administered in combination with antibodies, antibody fragments, and/or antibody analogs directed towards hWARS or in combination with hWARS proteins, peptides, and/or analogs in the treatment of infection by enteroviruses (such as EV-A71) and/or their sequelae.

Figure 4A:
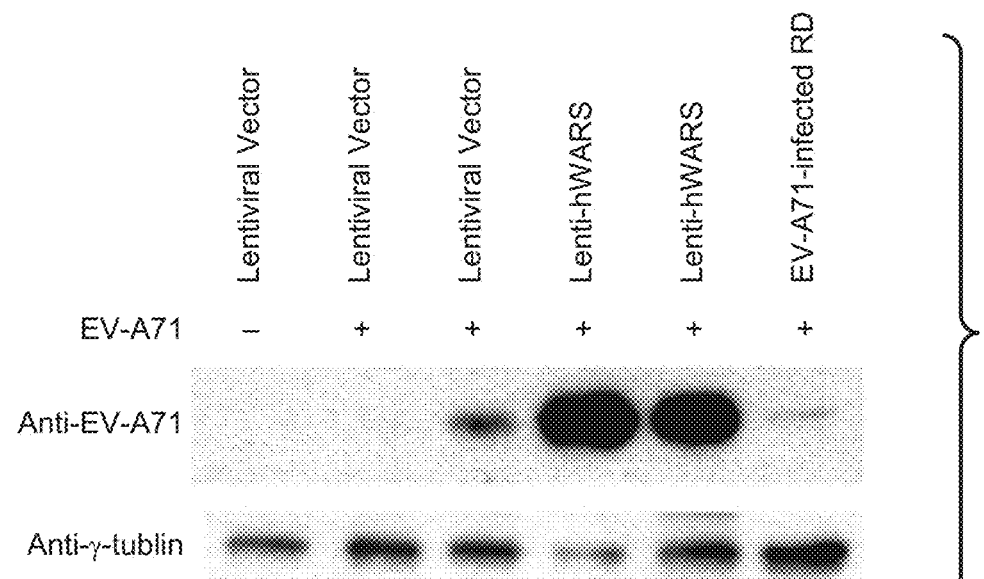
FIGS. 4A to 4D show results from EV-A71 infection of mouse cells overexpressing hWARS.
Figure 4B:
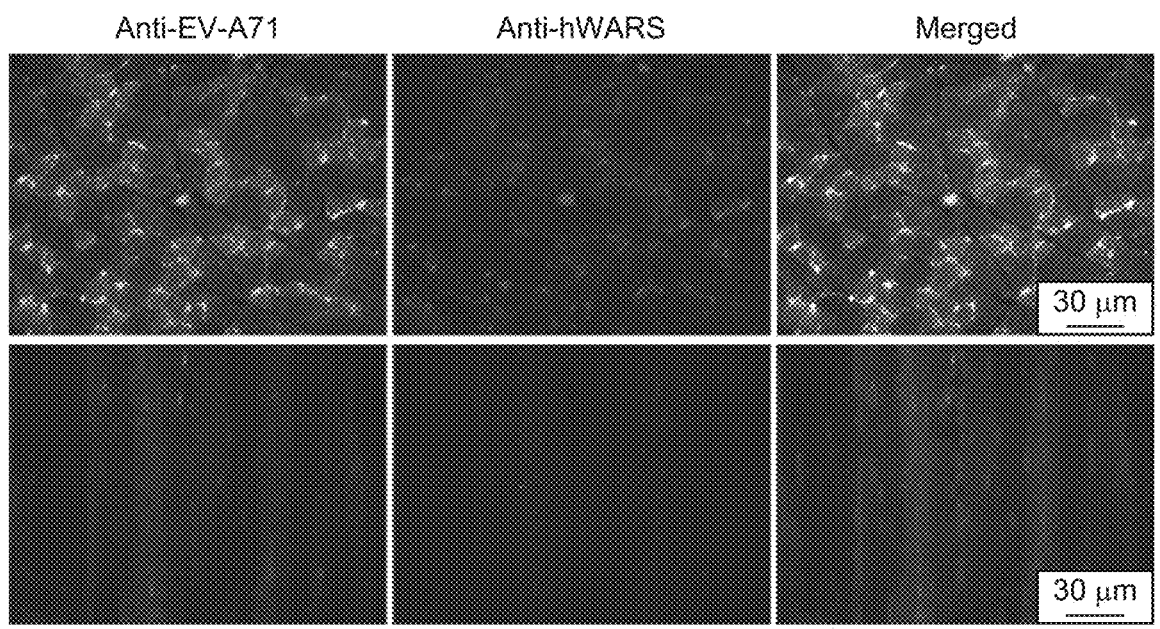
Figure 4C:
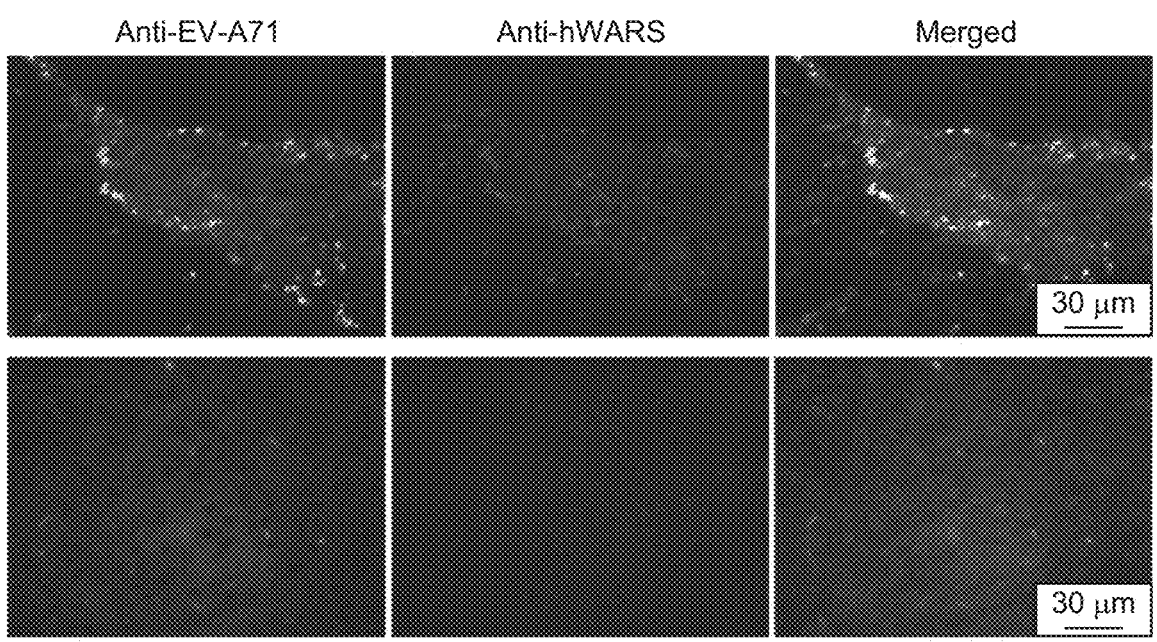
Figure 4D:
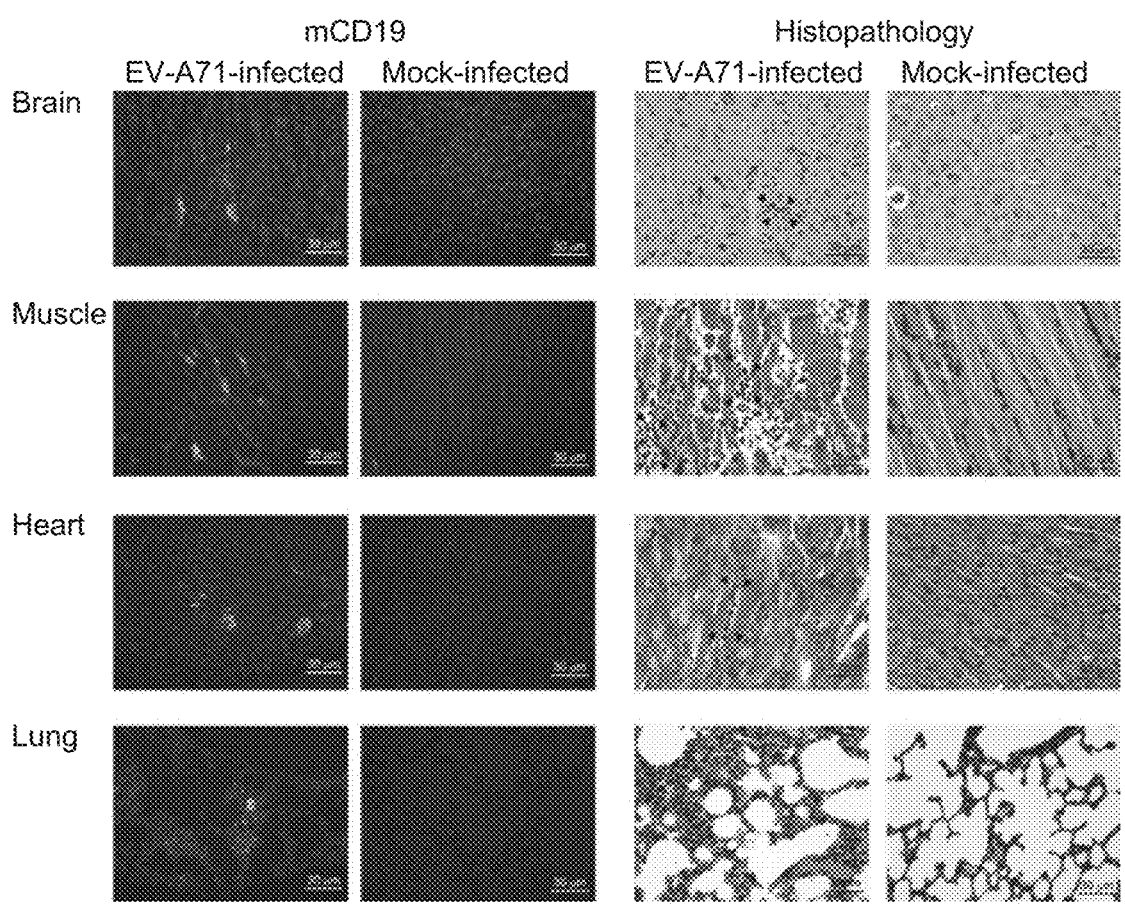

To determine if hWARS can act as a functional receptor for EV-A71 infection in vivo, the inventors developed a mouse model which overexpressed hWARS by a lentiviral vector (lenti-) expression system. Successful gene delivery by such a mechanism was first confirmed by the detection of hWARS expression in lenti-hWARS-transduced L929 cells. Subsequently Inventors transduced neonatal BALB/c mice with $10^6$ copies of lenti-hWARS (using empty lentiviral vector as a control) via intraperitoneal, intracerebral, and subcutaneous injection simultaneously. hWARS was allowed to be overexpressed for 5 days before the mice were challenged with EV-A71. As early as 5 days post-EV-A71 inoculation, Inventors detected EV-A71 proteins and RNAs in skeletal muscles and brains of mice transduced with lenti-hWARS (FIGS. 4A, 4B, and 4C). In contrast, viral protein and/or RNA was barely detectable or not detected in control mice transduced with empty lentiviral vector followed by EV-A71 inoculation. Pathologically, Inventors observed interstitial infiltration of inflammatory cells in various organs (FIG. 4D; left panels). The inventors also observed degeneration of neurons, which was consistent with the ataxia and paralysis observed with the EV-A71-inoculated lenti-hWARS-transduced mice. These findings indicate that such a mouse model can fully or partially recapitulate the neurological symptoms associated with EV-A71 infection in humans. Such a mouse model can serve as a research tool in the development of safe and effective therapies for enterovirus infection and/or prevention or treatment of neurological sequelae of enteroviral infection, and can also support the development of diagnostic tools.

Proinflammatory cytokines induced by early innate immune response often help to control virus replication and prime humoral and cell-based adaptive immune responses. During severe EV-A71 infection in human, a subset of proinflammatory cytokines, including IFNγ, is significantly elevated in patients with severe EV-A71 infections. These clinical observations corroborated with the findings that IFNγ can alter certain cell types' susceptibility to EV-A71.

The IFNγ-induced hyperexpression and membrane translocation of the novel EV-A71 cellular receptor, hWARS, which in turn sensitized cells that are normally non- or semi-permissive to infection, can provide a new model to study the EV-A71 pathogenesis. Blocking the accessibility of hWARS by specific antibodies or recombinant proteins (as noted above) can be potential treatment options for the EV-A71-associated severe neurological complications. Similarly, medicaments that incorporate such proteins, peptides, and/or compounds can be useful in treating or preventing enterovirus (for example, EV-A71) infection and/or its sequelae.

Inventors believe that the balance between T-helper1 activity and T-helper2 activity can play an important and previously undocumented role in the control of viral infection, and that the effectiveness of reducing IFNγ activity in reducing or eliminating enteroviral infection is due at least in part to alteration of this balance. Alteration of the balance between T-helper1 and T-helper2 activity can, therefore, provide a method for treating or preventing an enterovirus (for example, EV-A71) infection and/or sequelae of such an infection. This can, for example, be accomplished using compounds that interact with toll-like receptors, treatment with glucocorticoids, and treatment with CpG oligodeoxynucleotides, treatment with calcitriol, and/or treatment with other immune modulators. Similarly, Inventors believe that use of medicaments that incorporate such compounds can be useful in treating or preventing enteroviral infection and/or its sequelae.

It should be appreciated that each of the above described treatment modalities can be combined with one another in order to provide a combined and/or synergistic effect. Similarly, such treatment modalities can be used in conjunction with the administration of a preventative or therapeutic vaccine and/or antiviral compound directed to an enterovirus.

EXAMPLES

Cell Lines:

NT2 (ATCC), RD (ATCC) and its derivative cell clones were maintained in Dulbecco's Modified Eagle Medium (DMEM) (Life Technologies) supplemented with 10% (v/v) heat-inactivated fetal calf serum (FCS) (HyClone), 100 units/ml of penicillin, and 100 μg/ml of streptomycin (Life Technologies). Cells were selected and maintained in the same medium as described above with the addition of 1 μg/ml of puromycin. L929 cells were maintained in RPMI-1640 medium (Life Technologies) supplemented with FCS and antibiotics. All cell lines used were confirmed to be free of mycoplasma contamination using Plasmo Test (InvivoGen).

Mice:

Female BALB/c mice at 5 days of age were obtained from the Laboratory Animal Unit, the University of Hong Kong. The animals were housed in SPF-free facilities with 12 hours light-dark cycles together with lactating mothers. All animal-related experiments were performed according to the standard operating procedures as we previously described26 and approved by the University of Hong Kong Committee on the Use of Live Animals in Teaching and Research.

Production of shRNA Library and Stable Clones:

Feline immunodeficiency virus (FIV)-based shRNA library was produced. Briefly, 2 g of the shRNA library in lentiviral constructs (SBI) were co-transfected with 10 Lg of the pPACK packaging plasmid mix into HEK293T cells using Lipofectamine and Plus reagents according to the manufacturer's protocol (Invitrogen). At 24 and 72 hours after transfection, conditioned culture media were collected to harvest the packaged viruses. In parallel, GFP-packaged viruses were produced. The infectivity of the viruses was established based on the percentage of the GFP-transduced RD cells. One week after transduction, the cells were selected for three weeks in growth medium containing 1 μg/ml of puromycin. For independent validation, shRNA-expressing vector constructs (Mission shRNA) were purchased from Sigma. These shRNA-packaged viruses were generated in HEK293T cells using ViraPower™ Lentiviral Expression Systems (Invitrogen) according to the manufacturer's protocol.

shRNA-Based Screening:

shRNA-transduced RD cell clones were challenged with EV-A71 ($TCID_{50}$=1000). Four weeks after infection, small RNAs were harvested using mirVana™ small RNA isolation kit (Ambion). Five microgram of total RNAs were reverse transcribed into cDNAs in the presence of 10 μM of cDNA synthesis GNF primer (5'-ATTATTGTATCTGTGG-GAGCCTC-3') (SEQ ID NO. 1), 100 mM dithiothreitol, 10 mM of each dNTP, 1× reverse transcriptase buffer, and 200 U of SuperScript® III Reverse Transcriptase (Invitrogen). The reaction mixtures were incubated at 42° C. for 1 hour. The reaction was stopped by heat inactivation at 72° C. for 5 minutes. Half of the reaction mixture was then transferred to a tube containing 1×PCR reaction buffer, 20 mM of dNTP, 20 ipM of Fwd GNF primer (5'-TGCATGTCGC-TATGTGTTCTGGGA-3') (SEQ ID NO. 2) and 20 μM of Rev GNF primer (5'-ACAAAGCACTGGAAGC-TATCGAA-3') (SEQ ID. NO 3) and Advantage® HF2 Taq polymerase (Clontech).

PCR amplification of the shRNA target region was performed under the following conditions: Step 1: 94° C. for 4 minutes; Step 2: 94° C. for 30 second and then 68° C. for 1 minute; Step 3: Repeat Step 2 for 20 cycles; Step 4: 68° C. for 3 minutes. Aliquots were made by transferring 1 μl of the first round PCR products into 4 new tubes, each containing 1×PCR reaction buffer, 20 mM of dNTP, 20 ipM each of NRev GNF universal primer (5'-AAAGAATGCT-TATGGACGCTAGAA-3') (SEQ ID NO. 4) and NFwd-Bio primer (Biotin-5'-CTfCCTGTCAGA-3') (SEQ ID NO. 5) and Advantage® HF2 Taq polymerase (Clontech). PCR for biotin-labeling was performed under the following conditions: Step 1: 94° C. for 2 minutes, 50° C. for 2 minutes and then 68° C. for 1 minute; Step 2: 94° C. for 30 second and then 68° C. for 30 second; Step 3: Repeat Step 2 for 18 cycles; Step 4: 68° C. for 3 minutes. The PCR products were then gel purified using QIAquick PCR purification kit (QIAGEN) as described in the manufacturer's protocol. After purification, the PCR product was treated with Lambda exonuclease (NEB) at 37° C. for 2 hours to remove the non-biotinylated strand. The digested products were purified as described above and then quantified. Ten microgram of the purified products were hybridized on the GeneChip® Human Genome U133+2 Array (Affymetrix) using the Affymetrix hybridization buffer followed by staining with streptavidin-phycoerythrin (Molecular Probes). According to the standard Affymetrix protocol, the image of the processed chip was captured by scanner controlled by Affymetrix GCOS software. The signals were summarized for replicates with two or more replicate values above 100. The fold changes were determined based on the ratio of the signals between the mock and infected samples. Data have been deposited en toto into the Gene Expression Omnibus and are available under record series GEO accession number: GSE80407. Pathway analysis was done by using the Ingenuity program (QIAGEN).

Quantitative Polymerase Chain Reaction Analyses:

Total RNAs were isolated using mirVana miRNA isolation kit (Ambion). The RNAs were first quantified by NanoDrop® Spectrophotometer (ND-1000; Thermo Scientific). One microgram of the total RNAs were reverse transcribed as described above. qPCR was performed using FS Universal SYBR Green MasterRox (Roche) reaction mix with the temp-cycling condition of 15 second at 95° C. followed by 1 minute at 60° C. for 55 cycles in a 7900 Real Time PCR System (Applied Biosystems). EV-A71-infected samples' cDNAs were quantified using 300 nM each of forward and reverse specific primers (5'-CCCCT-GAATGCGGCTAATCC-3', SEQ ID NO. 6, and 5'-ACACGGACACCCAAAGTAGT-3', SEQ ID NO. 7). For different enterovirus serotype sample detection, forward and reverse specific primers (5'-GCCCCT-GAATGCGGCTAAT-3', SEQ ID NO. 8, and 5'-ATTGT-CACCATAAGCAGYCA-3', SEQ ID NO. 9) and a probe (5'FAM-CGGACACCCAAAGTAGTCGGTTCCG-1ABkFQ 3') (SEQ ID NO. 10) were used. A plasmid with the target 5'NCR sequence of 129 base pairs was used to generate the standard curve. Housekeeping gene GAPDH expression was also measured as an internal control using primers 5'-TCACCACCATGGAGAAGGC-3' (SEQ ID NO. 11) and 5'-GCTAAGCAGTTGGTGGTGCA-3' (SEQ ID NO. 12). The expression levels of host gene candidates were quantified using sequence-specific fluorescent DNA probes (WARS; Hs00188259_m1). After reverse transcription, the cDNAs were added to a reaction mixture containing the TaqMan universal PCR master mix (Applied Biosystems) and the TaqMan gene expression assay mix (inventoried for the corresponding genes; Applied Biosystems). Quantitative PCRs were carried out using the same conditions described above.

Confocal and Fluorescent Microscopic Analyses:

RD cells and their derivative knockdown cells were fixed in 4% paraformaldehyde with or without 0.1% triton X-100. After 1 hour blocking with 3% bovine serum albumin (BSA) at room temperature, the cells were stained with anti-EV-A71 antibodies (Millipore) and/or with anti-hWARS antibodies (Abcam) for 1 hour at room temperature as we previously described. 30 Unbound antibodies were washed away 6 times with PBS. Positively stained cells were detected by secondary IgG (H+L) antibodies conjugated either with Alexa Fluor 488 or Alexa Fluor 594 (Life Technology) for 30 minutes at room temperature. After 6 times of PBS washing, the stained cells were mounted onto glass slides with VECTASHIELD mounting medium with 4',6'-diamidino-2-phenylindole (DAPI) (Vector Lab) and examined with a Leica TCS-NT microscope (Leica Microsystem) or a LSM700 confocal microscope (Zeiss). For the staining of animal tissues, the tissue sections were first de-paraffinized and rehydrated, followed by treatment with Antigen Unmasking Solution (Vector Lab) to retrieve the antigens according the manufacturer's instructions. Detection of antigens was done under the same conditions as described above.

Virus Attachment Assays:

L929 cells transfected with hWARS, hSCARB2, hPSGL1 or empty plasmid control were mixed with high-titer EV-A71 ($TCID_{50}$=190,000), separately, at 4° C. for 2 hours. Unbound viruses were removed by washing with ice-cold PBS twice. The cells were than fixed in 4% paraformaldehyde for 15 minutes. After 1 hour of blocking with 3% BSA at room temperature, the cells were co-stained with anti-EV-A71 and anti-hWARS or anti-SCARB2 or anti-PSGL1 antibodies. Co-localization analyses were performed using the WCIF ImageJ bundle software (National Institutes of Health, Bethesda, MD, USA).

Western Blot Analyses:

Cell lysates or tissue extracts were resolved by sodium dodecyl sulfate (SDS)-polyacrylamide gel electrophoresis (PAGE). Proteins were transferred to polyvinylidene difluoride (PVDF) membrane by electroblotting (Hoefer) at a constant current of 150 mA overnight. Detection of antigens was performed using anti-EV-A71 (Millipore), anti-hWARS antibodies (Abcam), anti-hSCARB2 antibodies (Abcam), and anti-hPSGL1 antibodies (Abcam). As loading controls, the membranes were stripped with Restore Western blot stripping buffer (Pierce) before reprobing with anti-γ-tubulin antibodies (Sigma), anti-Na+/K+-ATPase antibodies (Abcam) and anti-GAPDH antibodies (Abcam).

In Vitro Pull-Down Assays:

Recombinant hWARS proteins were incubated with EV-A71 viruses under the following conditions: both recombinant hWARS and EV-A71 viruses were mixed in the presence of 0.1% Tween 20 at 4° C. overnight with shaking. The following day, anti-hWARS antibodies (Abcam) and agarose-conjugated secondary IgG (H+L) antibodies (Abcam) were added into the mixture and allowed to incubate for an additional 2.5 hours. After washing 6 times with buffer containing 50 mM $NaH_2PO_4$, 300 mM NaCl, and 20 mM imidazole pH 8.0, agarose-bound proteins were fractionated by SDS-PAGE and detected by Western blot analysis using anti-hWARS antibodies (Abcam) and anti-EV-A71 antibodies (Millipore).

Subcellular Fractionation:

Subcellular fractionation of RD and NT2 cells were performed using the Plasma Membrane Protein Extraction Kit (Abcam) following the manufacturer's protocol. Briefly, $10^8$ cells were harvested by scraping. The cells were washed once with 3 ml of PBS before lysis in 1 ml of the Homogenize Buffer. Lysed cells were mixed on ice by passing through a syringe 10 times. The supernatants were collected after sedimentation at 700×g for 10 minutes at 4° C. The cytoplasmic fraction (supernatant) and the total cellular membrane (pellet) fractions were further separated by centrifugation at 10,000×g for 30 minutes at 4° C. Plasma membrane proteins were further extracted by resuspending the total cellular membrane pellet in 200 μl of the Upper Phase Solution and 200 μl of the Lower Phase Solution. The complex was then incubated on ice for 5 minutes before centrifugation at 1000×g for 5 minutes at 4° C. The upper phase was collected and the steps were repeated by adding 100 μl Lower phase solution. The upper phase was collected and combined with the previously harvested upper phase.

The resultant was then diluted in 5 volumes of water and kept on ice for 5 minutes. The plasma membrane proteins were collected by centrifugation of the diluted upper phase at 10,000×g for 10 minutes at 4° C. 0.5% Triton X-100 in PBS was added to dissolve the plasma membrane protein pellets for Western blot analysis.

Animal Infection Model:

hWARS-expressing lentiviruses were generated using ViraPower™ Lentiviral Expression Systems (Invitrogen) as described above. The virus titers were first determined in L929 cells. Viruses (1×10$^6$) were concentrated by ultracentrifugation and then resuspended in 100 µl of PBS for intranasal, intravenous, and intraperitoneal injections under anesthesia using ketamine (100 mg/kg) and xylazine (10 mg/kg). Five days after transduction, the 10 day old mice were challenged again with EV-A71 (TCID$_{50}$=10000) using the same routes of delivery. Three to six mice from each group were sacrificed to harvest their heart, brain, muscles, kidney, lung, liver and spleen, respectively, at day 5 after virus inoculation. Four independent experiments were done. The collected organs were divided into different sets for qPCR, Western blot, immunohistochemical and histopathological analyses.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating or reducing susceptibility to an enterovirus infection of an animal comprising introducing a human tryptophanyl-tRNA synthetase (hWARS) blocking compound to the animal in an amount effective to reduce binding of enterovirus to hWARS at the surface of cells of the animal, wherein the enterovirus is selected from the group consisting of Enterovirus species A serotype EV-A71, Enterovirus species A serotype CV-A6, Enterovirus species A serotype CV-A8, Enterovirus species A serotype CV-A10, Enterovirus species A serotype CV-A16, Enterovirus species B serotype E-6, Enterovirus species B serotype E-11, Enterovirus species B serotype E-25, Enterovirus species B serotype E-30, and Enterovirus species D serotype D68, and wherein the hWARS blocking compound is selected from the group consisting of an anti-hWARS antibody and an antigen-binding anti-hWARS antibody fragment.

2. The method of claim 1, wherein the method of treating comprises treatment of a disease associated with an enterovirus infection selected from the group consisting of aseptic meningitis, pericarditis, myocarditis and hand, foot and mouth disease.

3. The method of claim 1, wherein the hWARS blocking compound is administered in lyophilized or dried form that is reconstituted prior to use or as an intravenous infusion.

4. The method of claim 1, wherein the hWARS blocking compound is administered to the animal at intervals ranging from three times a day to once weekly.

5. A method of treating or reducing susceptibility to an enterovirus infection of an animal comprising introducing a human tryptophanyl-tRNA synthetase (hWARS) blocking compound to the animal in an amount effective to reduce binding of enterovirus to hWARS at the surface of cells of the animal, wherein the enterovirus is selected from the group consisting of Enterovirus species A serotype EV-A71, Enterovirus species A serotype CV-A6, Enterovirus species A serotype CV-A8, Enterovirus species A serotype CV-A10, Enterovirus species A serotype CV-A16, Enterovirus species B serotype E-6, Enterovirus species B serotype E-11, Enterovirus species B serotype E-25, Enterovirus species B serotype E-30, and Enterovirus species D serotype D68, and wherein the hWARS blocking compound is selected from the group consisting of an anti-hWARS antibody, an antigen binding anti-hWARS antibody fragment, and a bispecific antibody having specificity for both hWARS and a co-receptor for the enterovirus.

6. The method of claim 5, wherein the co-receptor for the enterovirus is hSCARB2 or hPSGL1.

7. The method of claim 5, wherein the method of treating comprises treatment of a disease associated with an enterovirus infection selected from the group consisting of aseptic meningitis, pericarditis, myocarditis and hand, foot and mouth disease.

8. A method of treating or reducing susceptibility to an enterovirus infection of an animal comprising introducing a human tryptophanyl-tRNA synthetase (hWARS) blocking compound to the animal in an amount effective to reduce binding of enterovirus to hWARS at the surface of cells of the animal, wherein the enterovirus is selected from the group consisting of Enterovirus species A serotype EV-A71, Enterovirus species A serotype CV-A6, Enterovirus species A serotype CV-A8, Enterovirus species A serotype CV-A10, Enterovirus species A serotype CV-A16, Enterovirus species B serotype E-6, Enterovirus species B serotype E-11, Enterovirus species B serotype E-25, Enterovirus species B serotype E-30, and Enterovirus species D serotype D68, and wherein the method comprises a passive immunization, wherein the passive immunization comprises blocking binding of the enterovirus to hWARS at the surface of cells of the animal.

9. The method of claim 8, wherein the method of treating comprises treatment of a disease associated with an enterovirus infection selected from the group consisting of aseptic meningitis, pericarditis, myocarditis and hand, foot and mouth disease.

10. The method of claim 8, wherein the hWARS blocking compound is administered in lyophilized or dried form that is reconstituted prior to use or as an intravenous infusion.

11. The method of claim 8, wherein the hWARS blocking compound is administered to the animal at intervals ranging from three times a day to once weekly.

12. A method of treating or reducing susceptibility to an enterovirus infection of an animal comprising introducing a human tryptophanyl-tRNA synthetase (hWARS) blocking compound to the animal in an amount effective to reduce binding of enterovirus to hWARS at the surface of cells of the animal, wherein the enterovirus is selected from the group consisting of Enterovirus species A serotype EV-A71, Enterovirus species A serotype CV-A6, Enterovirus species A serotype CV-A8, Enterovirus species A serotype CV-A10, Enterovirus species A serotype CV-A16, Enterovirus species B serotype E-6, Enterovirus species B serotype E-11, Enterovirus species B serotype E-25, Enterovirus species B serotype E-30, and Enterovirus species D serotype D68, and wherein the hWARS blocking compound is an anti-hWARS antibody.

\* \* \* \* \*

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Synthetic cDNA Synthesis GNF primer

<400> SEQUENCE: 1
atttattgta tctgtgggag cctc                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic Forward GNF Primer

<400> SEQUENCE: 2
tgcatgtcgc tatgtgttct ggga                                          24

<210> SEQ ID NO 3
<211> LENGTH: 23
<212> TYPE: DNA
<213> ORGANISM: Artificial Sequence
<220> FEATURE:
<223> OTHER INFORMATION: Synthetic Reverse GNF Primer

<400> SEQUENCE: 3
acaaagcact ggaagctatc gaa                                           23

<210> SEQ ID NO 4
<211> LENGTH: 24
<212> TYPE: DNA
<213> ORGANISM: Artificial Sequence
<220> FEATURE:
<223> OTHER INFORMATION: Synthetic NRev GNF Universal Primer

<400> SEQUENCE: 4
aaagaatgct tatggacgct agaa                                          24

<210> SEQ ID NO 5
```

```
<211> LENGTH: 12
<212> TYPE: DNA
<213> ORGANISM: Artificial Sequence
<220> FEATURE:
<223> OTHER INFORMATION: Synthetic NFwd-Bio Primer
<220> FEATURE:
<221> NAME/KEY: misc_feature
<222> LOCATION: (1)..(1)
<223> OTHER INFORMATION: Biotin covalently coupled to 5' end of nucleic
      acid in use

<400> SEQUENCE: 5
cttcctgtca ga                                                            12

<210> SEQ ID NO 6
<211> LENGTH: 20
<212> TYPE: DNA
<213> ORGANISM: Artificial Sequence
<220> FEATURE:
<223> OTHER INFORMATION: Synthetic EV-A71 Forward Primer

<400> SEQUENCE: 6
cccctgaatg cggctaatcc                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic EV-A71 Reverse Primer

<400> SEQUENCE: 7
acacggacac ccaaagtagt                                                    20

<210> SEQ ID NO 8
<211> LENGTH: 19
<212> TYPE: DNA
<213> ORGANISM: Artificial Sequence
<220> FEATURE:
<223> OTHER INFORMATION: Synthetic Non-EV-A71 Serotype Enterovirus
      Forward Primer

<400> SEQUENCE: 8
gcccctgaat gcggctaat                                                     19

<210> SEQ ID NO 9
<211> LENGTH: 20
<212> TYPE: DNA
<213> ORGANISM: Artificial Sequence
<220> FEATURE:
<223> OTHER INFORMATION: Synthetic Non-EV-A71 Serotype Enterovirus
      Reverse Primer

<400> SEQUENCE: 9
attgtcacca taagcagyca                                                    20

<210> SEQ ID NO 10
<211> LENGTH: 25
<212> TYPE: DNA
<213> ORGANISM: Artificial Sequence
<220> FEATURE:
<223> OTHER INFORMATION: Synthetic Probe Sequence
<220> FEATURE:
<221> NAME/KEY: misc_feature
<222> LOCATION: (1)..(1)
<223> OTHER INFORMATION: Fluorescein-label for dye
<220> FEATURE:
<221> NAME/KEY: misc_feature
<222> LOCATION: (27)..(27)
```

```
<223> OTHER INFORMATION: 1ABkFQ Fluroescent tag

<400> SEQUENCE: 10
cggacaccca aagtagtcgg ttccg                                         25

<210> SEQ ID NO 11
<211> LENGTH: 19
<212> TYPE: DNA
<213> ORGANISM: Artificial Sequence
<220> FEATURE:
<223> OTHER INFORMATION: Synthetic GADPH Primer

<400> SEQUENCE: 11
tcaccaccat ggagaaggc                                                19

<210> SEQ ID NO 12
<211> LENGTH: 20
<212> TYPE: DNA
<213> ORGANISM: Artificial Sequence
<220> FEATURE:
<223> OTHER INFORMATION: Synthetic GADPH Reverse Primer

<400> SEQUENCE: 12
gctaagcagt tggtggtgca                                               20

<210> SEQ ID NO 13
<211> LENGTH: 27
<212> TYPE: DNA
<213> ORGANISM: Artificial Sequence
<220> FEATURE:
<223> OTHER INFORMATION: Synthetic shRNA (shWARS1) sequence for Sense
      Strand for targeting Human tryptophanyl-tRNA synthetase (WRS)
      mRNA, complete cds

<400> SEQUENCE: 13
ggacgacgac aagctcgagc agatcag                                       27

<210> SEQ ID NO 14
<211> LENGTH: 27
<212> TYPE: DNA
<213> ORGANISM: Artificial Sequence
<220> FEATURE:
<223> OTHER INFORMATION: Synthetic shRNA sequence (shWARS2)  for Sense
      strand for targeting Homo sapiens tryptophanyl-tRNA synthetase
      (WARS), mRNA

<400> SEQUENCE: 14
ccagaccatg catgtagtcc actccag                                       27
```